United States Patent
Gagnon et al.

(10) Patent No.: US 11,357,467 B2
(45) Date of Patent: Jun. 14, 2022

(54) MULTI-PASS COMPUTED TOMOGRAPHY SCANS FOR IMPROVED WORKFLOW AND PERFORMANCE

(71) Applicant: Accuray, Inc., Sunnyvale, CA (US)

(72) Inventors: Daniel Gagnon, Twinsburg, OH (US); Chuanyong Bai, Solon, OH (US); Zhicong Yu, Highland Hts., OH (US)

(73) Assignee: Accuray, Inc., Sunnyvale, CA (US)

( * ) Notice: Subject to any disclaimer, the term of this patent is extended or adjusted under 35 U.S.C. 154(b) by 63 days.

(21) Appl. No.: 16/694,192

(22) Filed: Nov. 25, 2019

(65) Prior Publication Data

US 2020/0170591 A1 Jun. 4, 2020

Related U.S. Application Data

(60) Provisional application No. 62/878,364, filed on Jul. 25, 2019, provisional application No. 62/743,796, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
None
See application file for complete search history.

(56) References Cited

U.S. PATENT DOCUMENTS

| 4,190,773 A | 2/1980 | Braden et al. |
| 5,615,279 A | 3/1997 | Yoshioka et al. |

(Continued)

FOREIGN PATENT DOCUMENTS

| DE | 10 2006 007058 A1 | 7/2007 |
| EP | 1062914 A1 | 12/2000 |

(Continued)

OTHER PUBLICATIONS

International Search Report and Written Opinion from PCT/US2019/063080 dated Mar. 16, 2020.

(Continued)

*Primary Examiner* — Hoon K Song
(74) *Attorney, Agent, or Firm* — Calfee, Halter & Griswold LLP

(57) ABSTRACT

An x-ray imaging apparatus and associated methods are provided to execute multi-pass imaging scans for improved quality and workflow. An imaging scan can be segmented into multiple passes that are faster than the full imaging scan. Data received by an initial scan pass can be utilized early in the workflow and of sufficient quality for treatment setup, including while the another scan pass is executed to generate data needed for higher quality images, which may be needed for treatment planning. In one embodiment, a data acquisition and reconstruction technique is used when the detector is offset in the channel and/or axial direction for a large FOV during multiple passes.

18 Claims, 14 Drawing Sheets

Related U.S. Application Data filed on May 6, 2019, provisional application No. 62/836,357, filed on Apr. 19, 2019, provisional application No. 62/836,352, filed on Apr. 19, 2019, provisional application No. 62/821,116, filed on Mar. 20, 2019, provisional application No. 62/813,335, filed on Mar. 4, 2019, provisional application No. 62/801,260, filed on Feb. 5, 2019, provisional application No. 62/800,287, filed on Feb. 1, 2019, provisional application No. 62/796,831, filed on Jan. 25, 2019, provisional application No. 62/773,700, filed on Nov. 30, 2018, provisional application No. 62/773,712, filed on Nov. 30, 2018.

(51) Int. Cl.

| | | |
|---|---|---|
| A61B 6/03 | (2006.01) | |
| A61B 6/06 | (2006.01) | |
| A61B 6/02 | (2006.01) | |
| A61N 5/10 | (2006.01) | |
| A61B 6/08 | (2006.01) | |
| G06T 7/30 | (2017.01) | |
| A61B 5/055 | (2006.01) | |
| A61B 6/04 | (2006.01) | |

(52) U.S. Cl.
CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | |
|---|---|---|
| 6,233,478 B1 | 5/2001 | Liu |
| 6,307,909 B1 | 10/2001 | Flohr et al. |
| 7,050,528 B2 | 5/2006 | Chen |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |
| 9,400,332 B2 | 7/2016 | Star-Lack et al. |
| 2003/0007601 A1 | 1/2003 | Jaffray et al. |
| 2003/0076927 A1 | 4/2003 | Shigeyuki et al. |
| 2004/0091079 A1 | 5/2004 | Zapalac |
| 2004/0102688 A1* | 5/2004 | Walker ................. A61B 6/4085 600/407 |
| 2004/0202360 A1 | 10/2004 | Besson |
| 2005/0053188 A1 | 3/2005 | Gohno |
| 2005/0251029 A1 | 11/2005 | Khamene et al. |
| 2006/0109954 A1 | 5/2006 | Gohno |
| 2006/0262894 A1 | 11/2006 | Bernhadt et al. |
| 2007/0127621 A1 | 6/2007 | Grass et al. |
| 2007/0189444 A1 | 8/2007 | Van Steven-Daal et al. |
| 2008/0112532 A1 | 5/2008 | Schlomka et al. |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2010/0046819 A1 | 2/2010 | Noo et al. |
| 2010/0142791 A1 | 6/2010 | Tsuji |
| 2010/0208964 A1 | 8/2010 | Wiegert et al. |
| 2011/0142312 A1 | 6/2011 | Toth et al. |
| 2012/0014582 A1 | 1/2012 | Schaefer et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2015/0297165 A1* | 10/2015 | Tanaka ................. A61B 6/5294 378/4 |
| 2015/0305696 A1* | 10/2015 | Yamakawa ............ A61B 6/466 378/19 |
| 2016/0016009 A1* | 1/2016 | Manzke ............... A61N 5/1065 382/132 |
| 2016/0120486 A1 | 5/2016 | Goto et al. |
| 2016/0262709 A1 | 9/2016 | Siewerdsen et al. |
| 2017/0000428 A1* | 1/2017 | Goto ...................... A61B 6/035 |
| 2017/0197098 A1 | 7/2017 | Hirasawa et al. |
| 2017/0205360 A1 | 7/2017 | Cinquin et al. |
| 2017/0278277 A1 | 9/2017 | Morf et al. |
| 2017/0332982 A1 | 11/2017 | Koehler et al. |
| 2018/0028143 A1 | 2/2018 | Wiggers et al. |
| 2018/0070894 A1 | 3/2018 | Osaki et al. |
| 2018/0192978 A1 | 7/2018 | Naylor |
| 2018/0345042 A1 | 12/2018 | Voronenko et al. |
| 2020/0121267 A1 | 4/2020 | Deutschmann |
| 2021/0165122 A1* | 6/2021 | Morton ................... H05G 1/70 |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.

(56) References Cited

OTHER PUBLICATIONS

International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scalel 1, Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,161 dated Sep. 13, 2021, 18 pages.
Office Action from U.S. Appl. No. 16/694,145 dated Mar. 17, 2021, 10 pages.
Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,202 dated Apr. 9, 2021, 12 pages.
Restriction Requirement from U.S. Appl. No. 16/694,210 dated Jun. 10, 2021, 6 pages.
Office Action from U.S. Appl. No. 16/694,218 dated Apr. 15, 2021, 7 pages.
Office Action from U.S. Appl. No. 16/694,230 dated Apr. 1, 2021, 6 pages.
Clackdoyle, et al., Data consistency conditions for truncated fanbeam and parallel projections, Med Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.

Kunze, et al.. Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging Physics in Medicine and Biology, pp. 6729-6748, vol. 51.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al.. Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions an Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Anas, et al. High-quality 3D correction of ring and radiant artifacts in flat panel detector-based cone beam volume CT imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, pp. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.

* cited by examiner

MULTI-PASS COMPUTED TOMOGRAPHY SCANS FOR IMPROVED WORKFLOW AND PERFORMANCE

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to computed tomography imaging, and, more particularly, to an apparatus and method for multi-pass scans associated with imaging, data reconstruction, and workflows, including when utilizing an off-centered (offset) detector during cone-beam computed tomography helical scans.

BACKGROUND

Computed tomography (CT) imaging, including cone-beam computed tomography (CBCT), is a valuable tool in radiotherapy. It can be used for patient positioning and dose calculation. It also has the potential to allow physicians to perform adaptive radiotherapy, including in the context of image-guided radiation treatment (IGRT). IGRT can make use of medical imaging technology, such as CT, to collect images of a patient before, during, and/or after treatment.

One popular data acquisition form is a circular scan, with a centered detector for small-object scans (e.g., head), and an off-centered (offset or shifted) detector in the channel direction for large object-scans (e.g., abdomen). For most radiotherapy systems, a circular scan is likely the only practical choice, as the gantry can only rotate in one direction for a limited number of degrees, thus preventing these machines from using a helical source trajectory. A helical scan can provide higher quality images with less artifacts, reduced scatter, and faster scanning when compared to circular scans, but view completion is much more complex.

CT images acquired on an IGRT system have two major applications: (a) registration with a planning CT image for patient treatment setup; and (b) adaptive planning and dose calculation. The requirements of the CT images for the two applications can be different. For registration and treatment setup, absolute accuracy in CT quantitation (such as CT numbers) is not as critical as for adaptive planning and dose calculation, yet relatively large axial field-of-view (FOV) is allowed for registration and setup accuracy.

BRIEF SUMMARY

In one embodiment, a method of collecting imaging data during a multi-pass scan includes moving a patient support relative to a rotatable gantry system during a first pass of an imaging scan, wherein a first radiation source and a radiation detector are coupled to the rotatable gantry system positioned at least partially around the patient support, receiving first projection data measured by the radiation detector during the first pass, moving the patient support relative to the rotatable gantry system during a second pass of the imaging scan, receiving second projection data measured by the radiation detector during the second pass, and reconstructing a patient image based on the first projection data and the second projection data.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
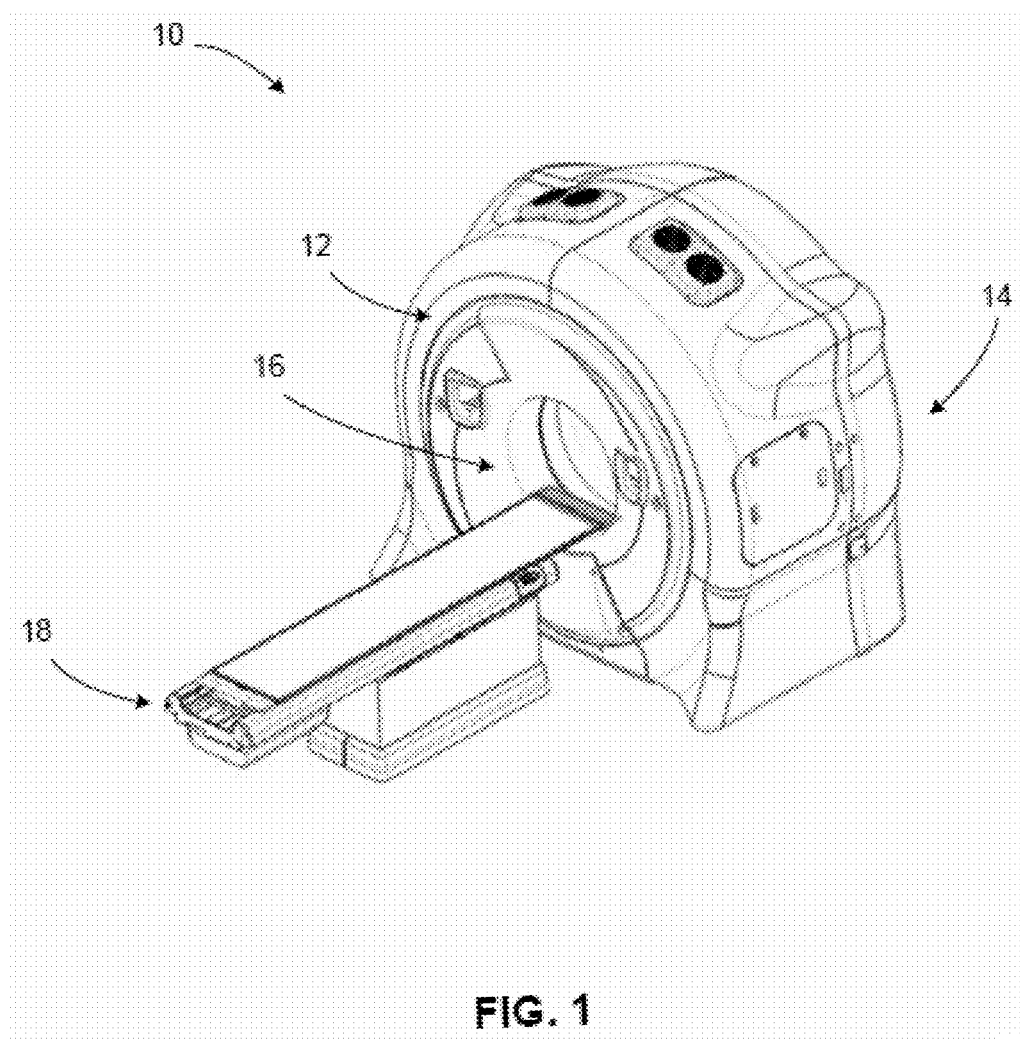
FIG. 1 is a perspective view of an exemplary x-ray imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multi-pass scans for improved workflow and/or performance. In some embodiments, a radiotherapy delivery device and method can make use of an integrated low-energy radiation source for CT for use in conjunction with or as part of IGRT. In particular, for example, a radiotherapy delivery device and method can combine a low-energy collimated radiation source for imaging in a gantry using rotational image acquisition along with a high-energy radiation source for therapeutic treatment. In various embodiments, the low-energy radiation source (e.g., kV) can produce higher quality images than via use of the high-energy radiation source (e.g., MV) for imaging. Images generated with kV energy can have better tissue contrast than with MV energy. High quality volume imaging can be needed for visualization of targets and organs-at-risk (OARS), for adaptive therapy monitoring, and for treatment planning/re-planning. In some embodiments, the kV imaging system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, etc.

In accordance with various embodiments, the x-ray imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

A helical scan trajectory can have several advantages in view of a circular scan. For example, cone-beam artifacts are reduced because a helical scan can provide more complete projection data for image reconstruction. Also, a helical scan can acquire projection data for a large longitudinal coverage with a narrow axial opening, which could substantially reduce scatter contamination in the projection data. Reconstructed images can have significantly improved image quality in terms of low frequency artifacts and result in greatly enhanced soft-tissue contrast. Furthermore, a helical scan can improve scan speed with a large pitch.

Figure 2:
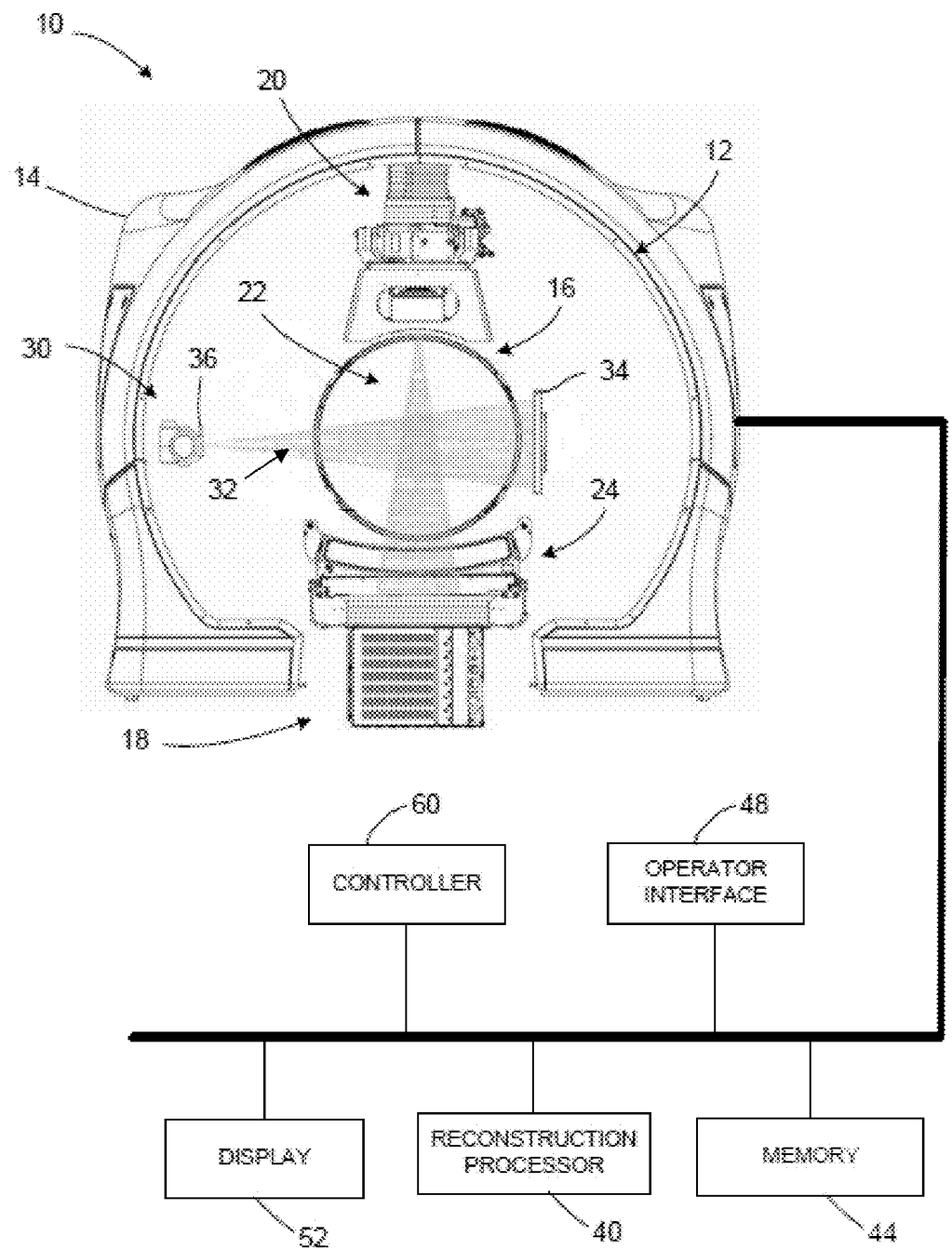
FIG. 2 is a diagrammatic illustration of an x-ray imaging apparatus integrated into an exemplary radiotherapy device in accordance with one aspect of the disclosed technology.

With reference to FIG. 1 and FIG. 2, an x-ray imaging apparatus 10 is shown. It will be appreciated that the x-ray imaging apparatus 10 may be associated with and/or integrated into a radiotherapy device (as shown in FIG. 2) that can be used for a variety of applications, including, but not limited to IGRT. The x-ray imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (e.g., x-ray) and an associated radiation detector while providing sufficient bandwidth for the high-quality imaging data received by the detector. A slip-ring gantry can eliminate gantry rotations in alternating directions in order to wind and unwind cables carrying the power and signals associated with the device. Such a configuration will allow for continuous helical (e.g., fan-beam, cone-beam, etc.) computed tomography, even when integrated into an IGRT system.

A patient support 18 or table/couch is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. In some embodiments, the patient support can also be moved in a limited range up and down, left and right once it is in the bore 16 to adjust the patient position for optimal treatment.

As shown in FIG. 2, the x-ray imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the x-ray source 30 rotates around and emits radiation toward the patient.

It will be appreciated that the x-ray detector 34 can take on a number of configurations without departing from the scope of the disclosed technology. As illustrated in FIG. 2, the x-ray detector 34 can be configured as a flat-panel detector (e.g., a multi-row flat panel detector). In accordance with another exemplary embodiment, the x-ray detector 34 can be configured as a curved detector. The detector 34 can be adjusted to an offset (i.e., shifted) position in the channel and/or axial direction.

Although FIGS. 1 and 2 depict an x-ray imaging apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which will be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector 34 (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task being carried out. The beam 32 can be shaped to be various shapes, including, for example, parallelograms. The beamformer 36 can be configured to adjust the shape of the radiation beam 32 by rotation and/or translation of x-ray attenuated material of the beamformer 36.

The collimator/beamformer 36 may be configured in a variety of ways that allow it to adjust the shape of the radiation beam 32 emitted by the x-ray source 30. For example, the collimator 36 can be configured to include a set of jaws or other suitable members that define and selectively adjust the size of an aperture through which the radiation beam from the x-ray source 30 may pass. In accordance with one exemplary configuration, the collimator 36 can include an upper jaw and a lower jaw, where the upper and lower jaws are movable in different directions (e.g., parallel directions) to adjust the size of the aperture through which the radiation beam from the x-ray source 30 passes, and also to adjust the beam position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2, the x-ray imaging apparatus 10 may be integrated with a radiotherapy device that includes a therapeutic radiation source 20 coupled to or otherwise supported by the rotatable gantry 12. In accordance with one embodiment, the therapeutic radiation source 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation. In one embodiment, the first source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the first source of radiation 20 has a higher energy level (peak and/or average, etc.) than the second source of radiation 30.

In one embodiment, the therapeutic radiation source 20 is a linear accelerator (LINAC) producing therapeutic radiation (e.g., MV source) and the imaging system comprises an independent x-ray imaging source of radiation producing relatively low intensity and lower energy imaging radiation (e.g., kV source). In other embodiments, the therapeutic radiation source 20 could be a radioisotope, such as, for example, Co-60, and it can generally have energy >1 MeV. The therapeutic radiation source 20 can emit one or more beams of radiation (indicated generally by 22) toward a region-of-interest (ROI) within a patient supported on the patient support 18 in accordance with a treatment plan. In some embodiments, the therapeutic radiation source 20 may be used for imaging.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a collimator. The collimator associated with the therapeutic radiation source 20 can be configured in a number of ways, similar to the collimator/beamformer 36 associated with the imaging source 30. For example, a collimator/beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, x-ray imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and/or any information obtained from these or other imaging modalities. In some embodiments, the x-ray imaging apparatus 10 can track in-treatment patient, target, or ROI motion.

A reconstruction processor 40 can be operatively coupled to detector 24 and/or x-ray detector 34. In one embodiment, the reconstruction processor 40 is configured to generate patient images based on radiation received by the x-ray detector 34 from the x-ray source 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The x-ray imaging apparatus 10 can include an operator/user interface 48, where an operator of the x-ray imaging apparatus 10 can interact with or otherwise control the x-ray imaging apparatus 10 to provide input relating to scan or imaging parameters and the like. The operator interface 48 can include any suitable input devices, such as a keyboard, mouse, voice-activated controller, or the like. The x-ray imaging apparatus 10 can also include a display 52 or other human-readable element to provide output to the operator of the x-ray imaging apparatus 10. For example, the display 52 can allow the operator to observe reconstructed patient images and other information, such as imaging or scan parameters, related to operation of the x-ray imaging apparatus 10.

As shown in FIG. 2, the x-ray imaging apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer 36 controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an x-ray imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an x-ray imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with x-ray imaging apparatus 10.

X-ray imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented.

It will be appreciated that the x-ray source 30 and the x-ray detector 34 can be configured to provide rotation around the patient during an imaging scan in a number of ways. In one embodiment, synchronizing the motion and exposure of the x-ray source 30 with the longitudinal motion of the patient support 18 can provide a continuous helical acquisition of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of radiotherapy devices 10 described above.

In one embodiment, the gantry 12 rotation speed, the patient support 18 speed, the beamformer 36 shape, and/or the detector 34 readout could all be constant during one or more passes of an image acquisition. In other embodiments, one or more of these variables could change dynamically during a pass or between passes of an image acquisition. The gantry 12 rotation speed, patient support 18 speed, beamformer 36 shape, and/or detector 34 readout can be varied to balance different factors, including, for example, image quality and image acquisition time.

In other embodiments, these features can be combined with one or more other image-based activities or procedures, including, for example, patient set up, adaptive therapy monitoring, treatment planning, etc.

Images are typically needed at different stages during radiation treatment. For example, in one treatment fraction, they are used for patient positioning at an early stage and for dose calculation at a later stage. Image quality requirements for patient positioning are less demanding than that on dose calculation. As mentioned above, images acquired on an IGRT system have two major uses: treatment setup (e.g., registration with a planning CT image for patient setup); and treatment planning (e.g., adaptive planning and/or dose calculation). The requirements of the images for these two applications can be different. For treatment setup, accuracy in image quantitation (such as CT numbers) is not as critical as for treatment planning. For example, a relatively large axial field-of-view (FOV) imaging may be sufficient for treatment setup, but not for treatment planning.

For a typical treatment, the total treatment time for each delivery fraction can include the time for the CT scan, CT reconstruction time, registration time of the CT image with the planning CT image, and treatment planning setup time. Conventional IGRT systems typically acquire one set of CT images for both treatment setup and treatment planning. In this manner, workflow for patient treatment may be less than optimal, since image requirements for treatment setup may be less.

Most IGRT systems with CT scan capabilities use CBCT scans with circular scans. When a relatively large axial range needs to be scanned, multiple circular scans can be performed with certain overlap between neighboring scans. If the image is also used for dose calculation, then sufficient scanning time is required for each circular scan to make the image accurate for dose calculation. The workflow includes waiting until all of the circular scans are finished and the resulting images are reconstructed before using the images for registration with the planning CT image and treatment setup. To improve the overall treatment workflow (minimizing the total treatment time), one approach includes reducing the number of circular scans or reducing the scanning time for each circular scan to achieve a satisfactory compromise among CT scanning range, scanning time, image quality, and the total registration/setup time.

An IGRT system with a helical CT scan capability can do a continuous scan in an axial direction. However, the overall workflow optimization may also require a compromise between the CT scanning range, pitch, total scanning time, image quality, and total registration/setup time.

As described herein, a multi-pass imaging scan can be used to optimize the workflow, including, for example, reducing the time required for the pre-delivery steps. The optimization can be applied via use of an IGRT system with circular and/or helical CT scan capabilities. Generally, the pre-delivery (and overall treatment) workflow can be improved by dividing or segmenting an imaging scan into multiple passes, each acquiring/generating different and/or complementary data that can be used at different steps of the workflow. Data can be used (e.g., for reconstruction) individually or in combination with earlier data. At least one pass is completed and utilized in less time than it would take to complete the full imaging scan. A first pass can be optimized to generate data needed for the initial steps of the workflow, which can include treatment setup (e.g., registration) and/or any other treatment pre-planning activities. Once the first pass is complete, the initial steps of the workflow can begin based on the first pass data at the same time a second pass of the imaging scan is executed. The second pass (and any other subsequent passes) can generate the remaining data needed for the remaining workflow steps. In some ways, the second pass may be considered as free time because the patient support has to be moved out of the gantry anyway—deferring some scanning for during this movement can be a better utilization of time.

In this manner, the initial steps of the workflow can be started and completed earlier in the workflow (i.e., rather than waiting for a complete scan). Furthermore, in various embodiments, total dosage can be maintained or even reduced via optimization. The first pass data can be used to determine scanning parameters for subsequent passes, further optimizing time, image quality, dosage, etc. In some embodiments, more than two passes can be utilized for various combinations and workflows with differing improvements.

Different scans of the multi-pass techniques may have different scan designs (e.g., different parameters). For example, dose, spectrum (dual energy), view sampling, detector position, detector resolution, collimation (e.g., $1^{st}$—narrow and $2^{nd}$—wide), energy, scan speed, (including, e.g., pitch), and/or type (e.g., helical, step-and-shoot, etc.), etc. may be varied between scans. Various combinations of these parameters differ in various embodiments.

The systems implementing the imaging scans can include a radiation source that can be in kV or MV, including with a corresponding kV or MV detector, as described above. The radiation source can also include different spectra, which can be, for example, a segmented or twin-beam like setup using an advanced collimator design. In some exemplary embodiments, the system may operate at up to 10 rpm for imaging and 6 rpm for treatment. Conventional CT is too fast (e.g., around 200 rpm) to implement these techniques. Various beam shapes, including fan beams and cone beams may be used.

In some embodiments, the first pass is performed with a relatively short scanning time, but with sufficient image quality for registration/treatment setup. The second pass can then be performed after the first pass and while the first pass data is processed (e.g., reconstructed and registered) for treatment setup to reduce workflow time. The first pass data can be reconstructed with a fast reconstruction algorithm and reconstruction parameters (such as image size) to minimize the reconstruction time. Data from all of the scan passes can be used to reconstruct a final image using advanced reconstruction algorithms for treatment planning (e.g., dose calculation and adaptive planning).

For example, in one embodiment, the first pass uses a sparse scan protocol that acquires fewer views of data than a conventional single scan while the second pass acquires data in another set of views that are interleaved with the views from the first pass. The joint data from the two passes will have combined (e.g., full) views that can be equivalent to or more than a conventional scan. In another embodiment, the second pass can use a different energy than the first pass and the joint data of the two passes not only provides sufficient angular resolution, but also provides spectral data. In another embodiment, the first pass and the second pass acquire different numbers of views, such that the joint data have evenly distributed views angularly or more dense views in some angular regions than others.

In some embodiments, the first pass image and the planning image, when registered and analyzed, can provide optimized scanning parameters for the second pass scan. For example, scan parameters can be optimized for speed of movement of the patient support, pitch, collimation, pulse rate of the imaging radiation, energy level (e.g., "color"), mA (e.g., number of x-rays), and/or gantry rotational speed. These parameters may also be varied for different axial regions during the same pass.

In various embodiments, movement of the source of imaging radiation 30 and the radiation detector 34 via the gantry 12 can be coordinated with movement of the patient support 18 to achieve a variety of imaging scan designs utilizing multiple scan passes. These movements can be controlled according to various scan protocols and the generated projection data processed (e.g., including via controller 60 and processor 40) to perform various steps of the treatment workflow, including, for example, image reconstruction, registration, related data processing, storage, communication, etc. within an IGRT system for treatment setup, treatment planning, and/or treatment delivery. For example, in one embodiment, step-and-shoot circular scans can be used. In another embodiment, movement of the patient support 18 and the gantry 12 may be coordinated with constant speeds to perform a helical scan. In another embodiment, the patient support 18 and/or the gantry 12 moves at a variable speed relative to the other. Speeds of the patient support 18 and the gantry 12 can be varied such that the time required to complete the first pass is less than the time required to complete the second pass, including creating various pitches of a helical scan or step distances of a circular scan.

For example, in one embodiment, a first pass of an imaging scan is a fast helical CT scan and the resulting image is reconstructed with sufficient image quality for treatment setup (e.g., registration). While the image is sent to the workstation for treatment setup, a second pass of the imaging scan is another helical CT scan performed by reversing the patient table moving direction. In this embodiment, the registration/treatment setup and the second pass of the imaging scan can happen simultaneously, reducing the total workflow time as compared to the conventional approach of acquiring one set of high-quality CT images for treatment setup and treatment planning (for each treatment fraction).

In this embodiment, the second pass can have the same scanning range as the first pass and the total patient dose can be the same as or lower than the conventional approach of acquiring one set of CT images during one pass.

In some embodiments, from the registration and/or setup result using the first pass data, the second pass scanning parameters may be adjusted, including, for example, limited to only scan the axial range of interest, which may be one segment or multiple segments.

In other embodiments, the first pass may also be used to adjust the imaging dose at different axial regions during the second pass, optimizing the dose distribution in the scan range for optimal image quality in regions where attenuation is more, while the total patient dose remains the same.

In some embodiments, from the registration results with the planning CT and/or the treatment pre-planning results using the first pass data, the second pass may use different scan parameters, including, for example, a different or varying pitch size in different axial ranges of the second pass, when higher resolution in certain axial ranges is desired.

In other embodiments, a multi-pass imaging scan can be used to generate high quality images quicker, including, for example, by starting reconstruction of the first pass data during the second pass, even if treatment setup is not started until completion of the imaging scan.

For example, this technique may be utilized for generating spectral images. Two or more helical scan passes of different tube energies can generate data/images from the multiple CT passes that can be used to generate spectral images, including electron density images, material decomposed images, etc. In one embodiment, the second pass can use a different kV energy than the first pass so that the two scans can allow spectral CT reconstruction. The resulting spectral CT can then be used to improve dose calculation and adaptive planning.

Figure 3:
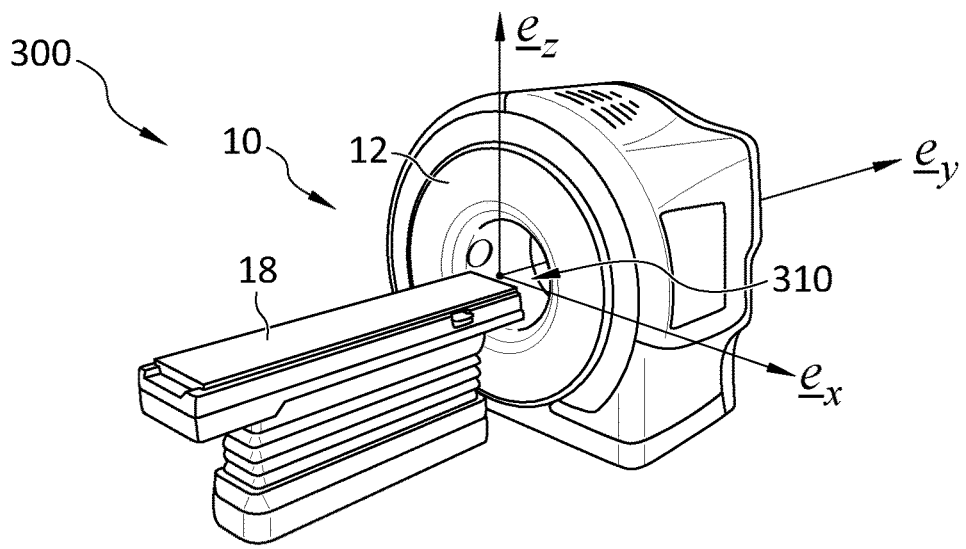
FIG. 3 is an illustration of an exemplary x-ray imaging apparatus shown with a world coordinate system defined.

With reference to FIG. 3, an illustration 300 of an x-ray imaging apparatus 10 is shown with a world coordinate system 310 defined. The origin, denoted as O, is the isocenter of the gantry 12 and the unit vectors associated with the x-, y-, and z-axes are shown as $\underline{e}_x$, $\underline{e}_y$, and $\underline{e}_z$, respectively. Viewing from the front of the gantry 12, the x-axis $\underline{e}_x$ is horizontal and points to the right, the y-axis $\underline{e}_y$ points into the gantry plane, and the z-axis $\underline{e}_z$ is vertical and points to the top. The x-, y-, and z-axes follow the right-hand rule.

Figure 4:
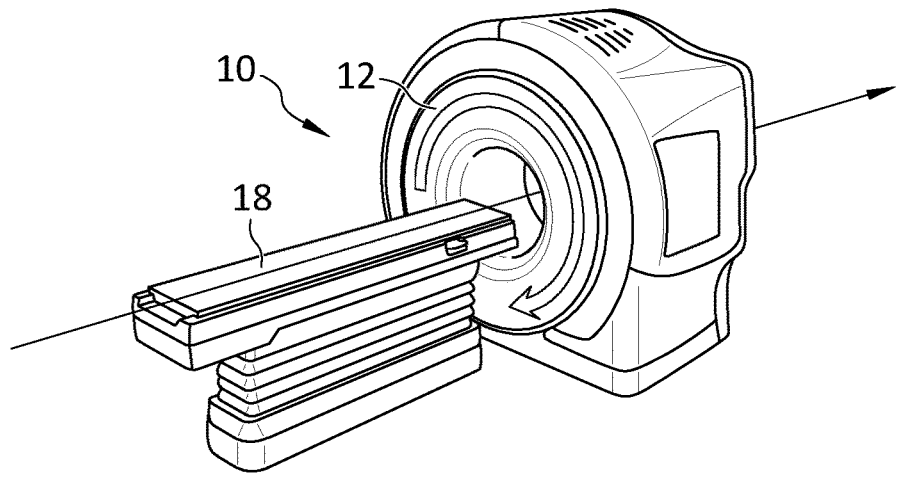
FIG. 4 is an illustration of an exemplary x-ray imaging apparatus shown with a patient support moving into a gantry during one scan pass.
Figure 5:
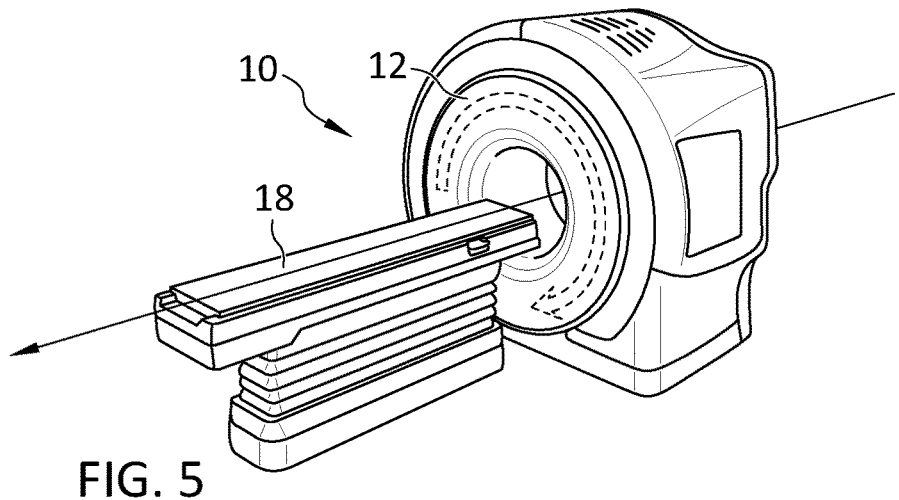
FIG. 5 is an illustration of an exemplary x-ray imaging apparatus shown with a patient support moving out of the gantry during another scan pass.

In an exemplary embodiment, the x-ray source 30 rotates clockwise when viewing from the front of the gantry 12. FIGS. 4-5 illustrate the movements of the gantry 12 and the patient support 18 during exemplary passes of an imaging scan. In particular, during the first pass of a dual-helical scan, the patient support 18 moves into the gantry 12 (along the y-axis while $\underline{e}_y$) the gantry rotates in an exemplary clockwise direction (around the y-axis $\underline{e}_y$) when looking into the gantry 12. During the second pass of the dual-helical scan, the patient support 18 moves out of the gantry 12 while the gantry rotates in the same exemplary clockwise direction. During the imaging scan, as discussed in more detail below, the data acquisition in the axial direction may be offset. In other embodiments, any number of passes may be used to complete an imaging scan.

In one embodiment, a dual-pass helical scan protocol can be utilized on an IGRT system with helical scan capability for improved workflow. In particular, after a patient is positioned on the patient support 18, a first pass helical scan is performed while the patient support 18 moves into the gantry 12 (e.g., as shown in FIG. 4), generating first pass projection data. Reconstruction of the first pass projection data into a first patient image can be concurrent with the first pass. A second pass helical scan is performed after the first pass by reversing the patient support 18 moving direction so that the patient support 18 moves out of the gantry 12 (e.g., as shown in FIG. 5), for example, while the other scanning parameters can be kept the same, generating second pass projection data. The first patient image from the first pass helical scan can be used for registration with the planning image and treatment setup while the second pass helical scan is performed, reducing the total time for the imaging scan and treatment setup, and in turn, improving the overall treatment workflow.

In another embodiment, a dual-pass helical scan protocol can be utilized on an IGRT system with helical scan capability for differential axial scanning optimization. In particular, a first pass helical scan is performed while the patient support 18 moves into the gantry 12 (e.g., as shown in FIG. 4), generating first pass projection data. Reconstruction of the first pass projection data into a first patient image can be concurrent with the first pass. After the first scan, the first patient image is registered with the planning CT and axial regions are identified for better resolution or improved statistics. This information can be used to set or adjust the scan parameters for a second pass helical scan while the patient support 18 moves out of the gantry 12 (e.g., as shown in FIG. 5). The identified regions can have the desired resolution and statistics to improve the accuracy for treatment planning, including, for example, dose calculation and adaptive planning.

In another embodiment, a multi-pass helical scan protocol can be utilized on an IGRT system with helical scan capability for spectral CT imaging. In particular, a first pass helical CT scan is performed while the patient support 18 moves into the gantry 12 (e.g., as shown in FIG. 4) using one tube energy and another pass of the helical CT scan while the patient support 18 moves out of the gantry 12 (e.g., as shown in FIG. 5) uses a different tube energy. The multiple passes provide data for spectral CT image reconstruction. The resulting spectral CT images can be used for treatment planning, including, for example, accurate dose calculation and adaptive planning.

Figure 6:
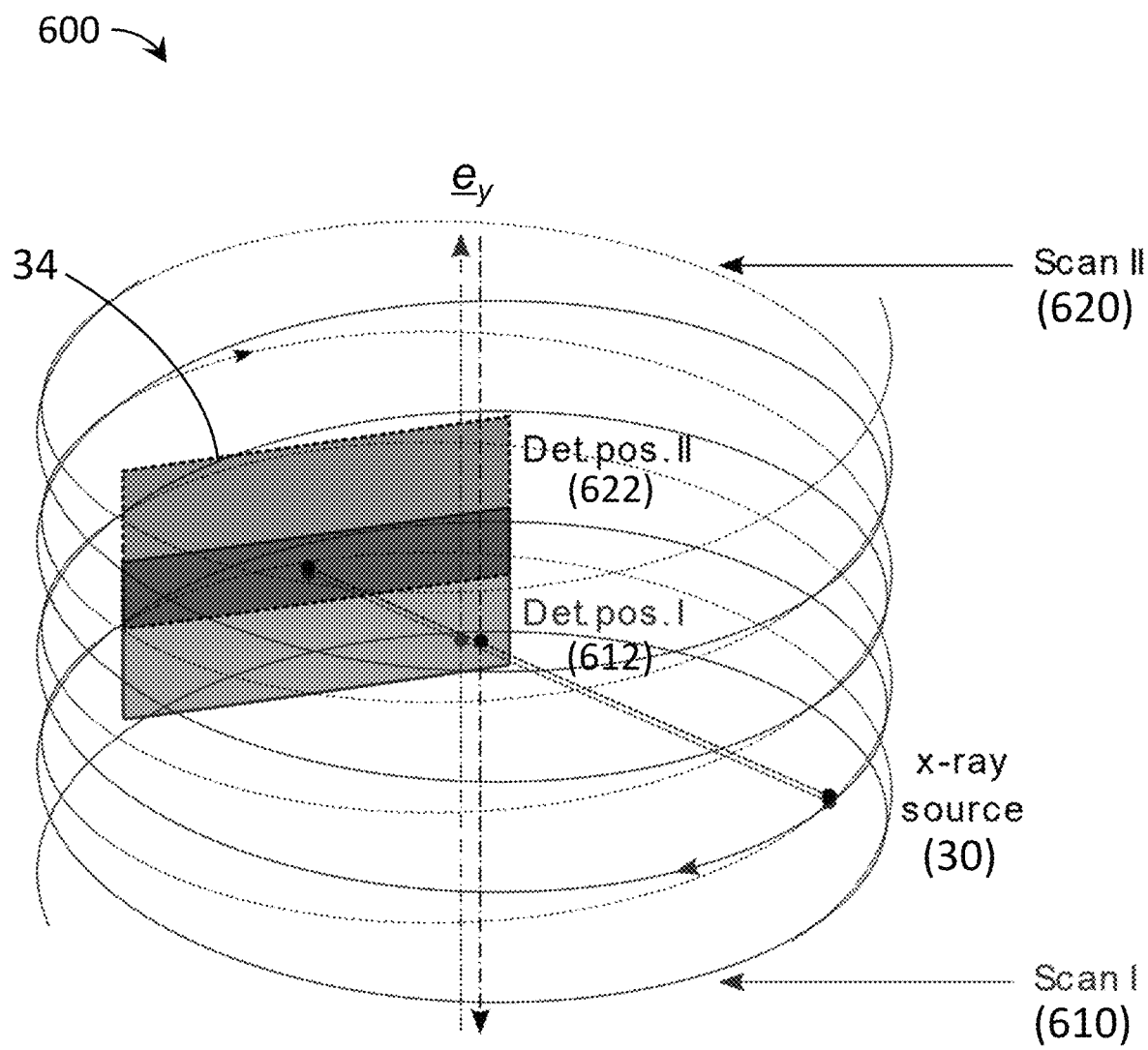
FIG. 6 is an illustration of exemplary trajectories associated with two interleaved scans during a dual-pass helical scan protocol with a large pitch for fast scanning.

In another embodiment, with additional reference to FIG. 6, a dual-pass helical scan protocol can be utilized with a large pitch for fast scanning. In this embodiment, a beamformer opening and detector active area can be one-sided with a very large pitch, such that during the second pass the beamformer opening and detector active area is on the other side relative to the first pass with the same pitch. Exemplary imaging scan design 600 shows the relative positions of a radiation source 30 and a radiation detector 34 during two passes of an imaging scan. In particular, a first pass helical CT scan 610 (Scan I) of an imaging scan is performed while the patient support 18 moves into the gantry 12 (e.g., as shown in FIG. 4) exposing the detector 34, shown at a first detector position 612 (Det. Pos. I). A second pass helical CT scan 620 (Scan II) of the imaging scan is performed while the patient support 18 moves out of the gantry 12 (e.g., as shown in FIG. 5) exposing the detector 34, shown at a second detector position 622 (Det. Pos. II). A large pitch is used for each of the two passes 610, 620 of the imaging scan, but the detector 34 and source 30 are shifted in the axial direction (along the y-axis $\underline{e}_y$) during the second pass 620 relative to the first pass 610 so the data from the two passes can be interleaved. When the data of the dual passes 610, 620 are used jointly, data sufficiency of the complete imaging scan is improved when compared to each of the two passes 610, 620, allowing for high quality image reconstruction. However, the first pass 610 with a large pitch allows for a faster (and earlier) scan and reconstruction, which can improve the workflow, for example, when the first pass 610 data is used for treatment setup during the second pass 620, thereby reducing the workflow and total treatment time. In different embodiments, the CT scanning system can be a cone-beam CT system with a flat-panel CT detector, a conventional multi-detector CT system, a single row CT system, etc.

In another embodiment, two passes of an imaging scan may include an offset detector in the scan design. Cone-beam CT (CBCT) is a prevalent imaging tool for IGRT. A typical CBCT system employs a flat panel detector 34, which is usually not large enough to encompass the entire cross section of a patient. An off-centered or offset detector can be used for circular scans with a large FOV. Using an off-centered detector configuration during a helical scan includes substantially more lateral data truncation. Due to such severe lateral data truncation, image quality is largely dependent on the helical pitch. Compared to helical scans without lateral data truncation, the maximum viable pitch of laterally truncated helical scans drops considerably, and so does the scan speed.

In this embodiment, a two-pass imaging scan for data acquisition consists of two helices. In the first pass, the patient support 18 moves into the gantry 12 (e.g., as shown in FIG. 4) with the detector 34 shifted to one lateral side. In the second pass, the patient support 18 moves out of the gantry 12 (e.g., as shown in FIG. 5) with the detector 34 shifted to the opposite side. The lateral detector translation between the two helices are designed for improved data availability for image reconstruction. Data acquired from the first pass might be reconstructed for patient positioning, whereas data from both passes can be used for an improved image reconstruction that is qualified for dose calculation. In various embodiments, this type of two-pass helical imaging scan design may be referred to as a double-helix trajectory. However, this double-helix trajectory requires a dedicated image reconstruction algorithm.

Figure 7:
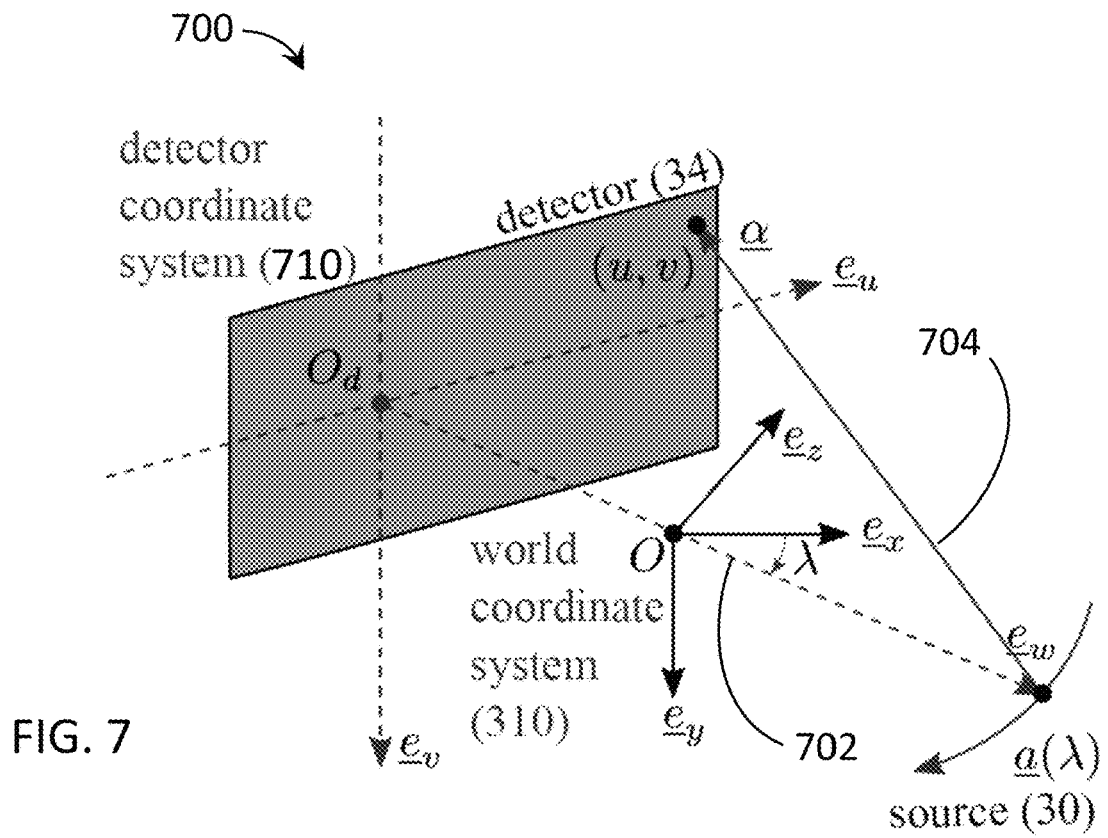
FIG. 7 is an illustration of the 3D geometry of an exemplary data acquisition system.
Figure 8:
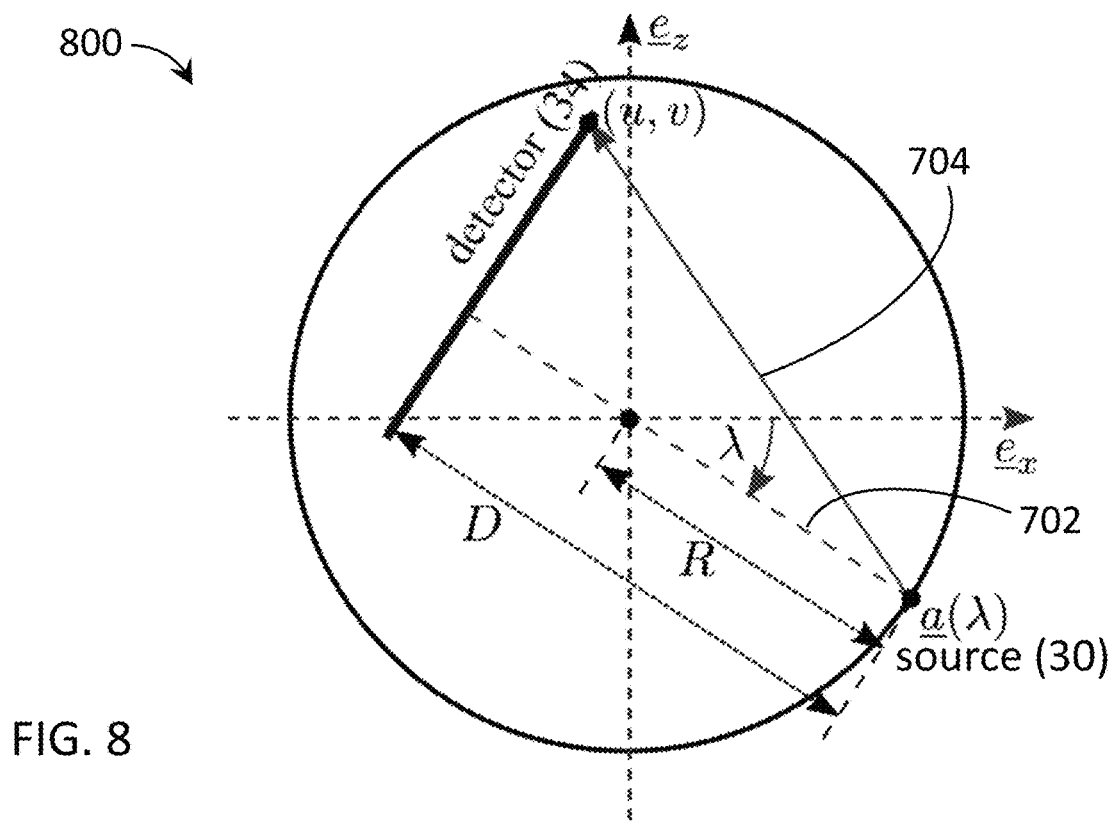
FIG. 8 is an illustration of the geometry of a data acquisition system in an exemplary (x, z)-plane.

The geometry of an exemplary data acquisition system for this embodiment is shown in FIGS. 7 and 8. As introduced in FIG. 3, the world coordinate system 310 is spanned by the (x, y, z) axes. FIG. 7 shows an illustration 700 of the 3D geometry of the exemplary data acquisition system. FIG. 8 shows an illustration 800 of the geometry of the data acquisition system in an exemplary (x, z)-plane. In an exemplary embodiment, the x-ray source 30 rotates clockwise when viewing from the front of the gantry 12. The view angle, $\lambda$, is defined as the angular distance from the x-axis $\underline{e}_x$ to the virtual line 702 connecting the source 30 and the rotation axis in a clockwise fashion when looking from the front of the gantry 12, with its vector position denoted as $\underline{a}(\lambda)$. The rotation axis is along the world coordinate y-axis $\underline{e}_y$. The detector 34 is positioned such that it is perpendicular to the plane defined by the source 30 and the rotation axis, its channels are parallel to the rotation axis, and its rows are perpendicular to the rotation axis. The piercing point of line 702 connecting the source 30 and the iso-center O at the detector 34 is defined as the origin of a detector coordinate system 710, which is denoted by $O_d$.

As shown in FIG. 7, two coordinate systems are involved with the exemplary data acquisition system. In particular, the data acquisition makes reference to the world coordinate system 310 with origin at O and the detector coordinate system 710 with origin at $O_d$. As introduced above, the detector coordinate system 710 is defined by basis vectors $\underline{e}_u$ (in the channel direction), $\underline{e}_v$ (in the row direction) in the detector 34 plane, and $\underline{e}_w$ (perpendicular to the detector 34 plane and pointing from $O_d$ to $\underline{a}$). Here, $O_d$ is defined as the piercing point on the detector 34 of the line 702 connecting the source 30 (with vector position $\underline{a}(\lambda)$) and O extended to the detector 34, along $\underline{e}_w$. Whereas $\underline{\alpha}(\lambda, u, v)$ is a unit vector 704 pointing from the source 30 vector position $\underline{a}(\lambda)$ to the detector 34 cell located at coordinates [u, v] in the detector coordinate system 710.

FIG. 8 illustrates the geometry 800 of the data acquisition system in an exemplary (x, z)-plane. The x-ray source 30 is located in the (x, z) plane and rotates clockwise around the y axis with a source-to-isocenter distance (SID) denoted by R. The view or rotation angle, denoted by $\lambda$, is defined as the clockwise angular distance from the x axis. The x-ray source 30 is denoted by $a(\lambda)$. The detector 34 is placed 180° apart from the x-ray source relative to the rotation axis with a source-to-detector distance (SDD) denoted by D. The detector 34 is perpendicular to the plane connecting the source 30 and y axis, with its channels being parallel to the y-axis. The detector plane is indexed by the (u, v)-coordinate system, with u for the detector channel position and v for the detector row position.

In this system, the x-ray detector 34 is an exemplary flat panel detector, and the 2D panel is spanned by the basis vectors $\underline{e}_u$ and $\underline{e}_v$, with $\underline{e}_u$ for the channel direction and $\underline{e}_v$ for the row direction. The v axis points to the same direction as the y axis, and the u axis points to the same direction as the rotation angular velocity. To extend the detector coordinate system to 3D, reference can be made to the w axis such that (v, u, w) axes follow the right-hand rule.

Figure 9A:
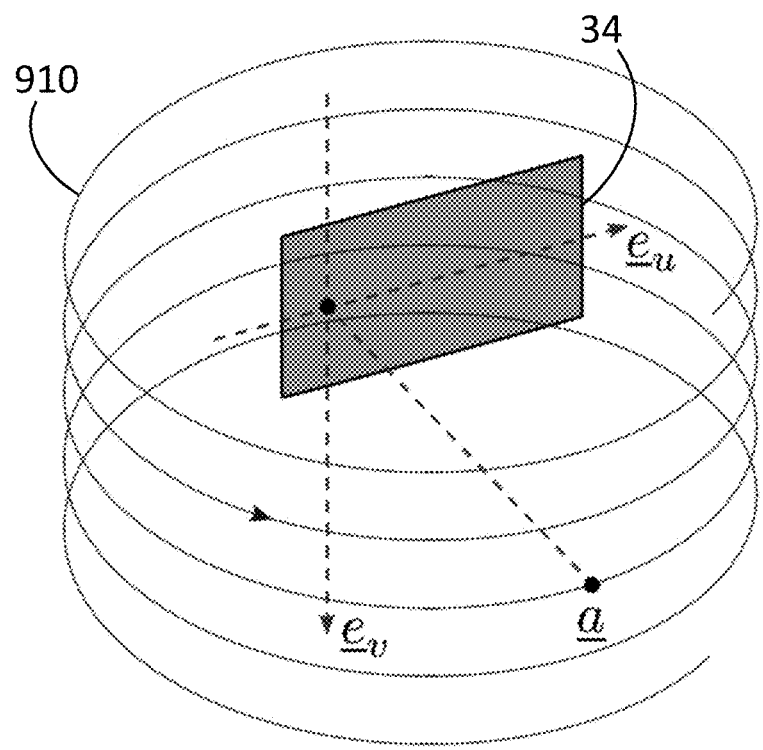
FIG. 9A is an illustration of an exemplary scan trajectory and offset detector position during a left-handed helix.
Figure 9B:
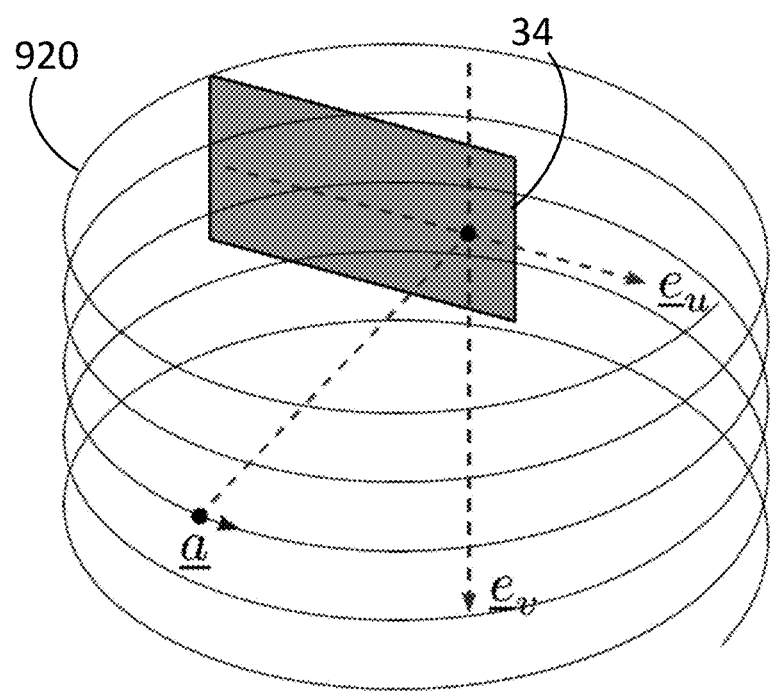
FIG. 9B is an illustration of an exemplary scan trajectory and offset detector position during a right-handed helix.

As described above, the double-helix scan design includes two complementary passes with a helical trajectory. FIG. 9A illustrates the trajectory of an exemplary left-handed helix (LHH) 910 and FIG. 9B illustrates the trajectory of an exemplary right-handed helix (RHH) 920, both shown with the detector 34 offset. The LHH 910 is formed by moving the patient support (not shown) into the gantry with the detector 34 shifted to +u-axis, whereas the RHH 920 is formed by moving the patient support out of the gantry with the detector 34 shifted to −u-axis. As shown in this embodiment, the off-centered detector 34 is large enough that the center x-ray (through the y axis) is detected and projections to the end of the shifted direction are not truncated. The pitches of the two helices 910, 920 can be different in general, but are shown here as being the same.

Regarding image reconstruction, it can be shown that there is only one π-line available for a point inside the convex hull of a helix, and that exact image reconstruction of points along a π-line is possible if the point is visible along the entire π-line segment. For a typical helical scan with no data truncation in the lateral direction, this condition is satisfied as long as the detector is large enough to contain the Tam-Danielsson (TD) window in the axial direction. This condition is not satisfied for a large amount of points in the scan field-of-view (SFOV) of a helical scan with an off-centered detector.

Figure 10:
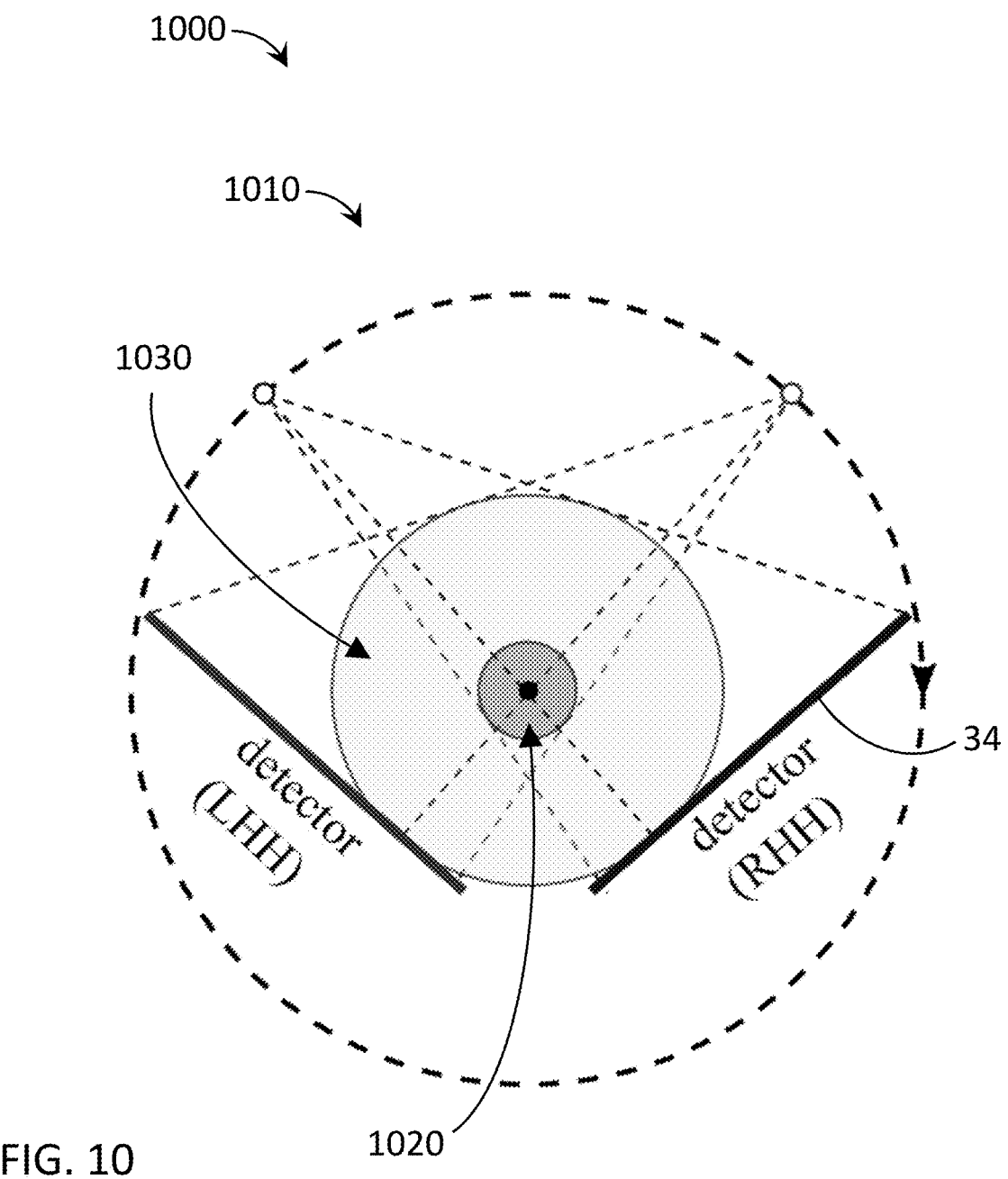
FIG. 10 is an illustration of the data availability during the scans shown in FIGS. 9A and 9B in an exemplary transverse plane.

Considering the exemplary double-helix scan design with the trajectories 910, 920 shown in FIGS. 9A and 9B, an illustration 1000 of data availability in an exemplary transverse plane is shown in FIG. 10. Depictions of the detector 34 during the exemplary left-handed helix (LHH) 910 pass and the exemplary right-handed helix (RHH) 920 pass are shown superimposed in the same transverse (x, z)-plane 1010. The SFOV is composed of a fully illuminated region 1020 and a partially illuminated region 1030. By construction, only the fully illuminated region 1020 is entirely visible at all azimuth angles, whereas the partially illuminated region 1030 is only visible by some azimuth angles. For a single helical scan with an off-centered detector, it can be shown that a good number of points in the partially illuminated region 1030 may not be entirely visible along their unique π-line segments, and thus cannot be exactly and stably recovered. It can also be shown that for such a trajectory with a large pitch, some points do not even have 180 degrees of data (relative to the point itself) for back-projection, which can pose even more difficulty in the reconstruction task due to the limited angle problem.

The limited angle problem can be avoided in the double-helix trajectory and thus relaxes the pitch requirement as compared to the situation of a single helix. One criteria of the pitch selection for the double-helix trajectory is that, for any point in the ROI, there is always a large enough azimuth angular range such that 180 degrees of data are available for back-projection.

Based on the above observation, in this embodiment, the reconstruction algorithm includes back-projecting all available data with a weighting mechanism such that all back-projection weightings at the same azimuth angle and the conjugate azimuth angle are normalized to 1. Such a weighting mechanism can be achieved via a pair of weighting functions denoted as $w^L$ and $w^R$, for the LHH and RHH respectively. The reconstruction algorithm is based on a general filtered back-projection (FBP) framework. Let $\hat{f}^L(\underline{x})$ and $\hat{f}^R(\underline{x})$ be the reconstructed images using data from the LHH and RHH, respectively. Let $\hat{f}(\underline{x})$ be the final reconstruction result.

The LHH reconstruction is described below in equation 1:

$$\hat{f}^L(\underline{x}) = \int_{\Lambda(\underline{x})} d\lambda \frac{1}{(\underline{a}(\lambda) - \underline{x}) \cdot \underline{e}_w} w^L(\lambda, \underline{x}) g_H^L(\lambda, u^*, v^*), \quad (1)$$

where (u*, v*) is the piecing point of the x-ray through x at the detector 34. The term $g_H^L$ in equation 1 is defined as below in equation 2:

$$g_H^L(\lambda, u, v) = h_H(u) * g_{CB}^{L'}(\lambda, u, v), \quad (2)$$

with $h_H(u)$ being the Hilbert transform, and according to equation 3:

$$g_{CB}^{L'}(\lambda, u, v) = \frac{D}{\sqrt{D^2 + u^2 + v^2}} \frac{\partial \hat{g}^L(\lambda, u, v)}{\partial \lambda} \bigg|_{\alpha \text{ fixed}}. \quad (3)$$

Here $\underline{\alpha}(\lambda, u, v)$ is the unit vector pointing from the source $\underline{a}(\lambda)$ to the detector point (u, v), $\hat{g}^L(\lambda, u, v)$ is the projection data with the laterally truncated data estimated using neighboring rotations by a known method and $g_{CB}^{L'}$ is view-dependent differentiation that can be implemented using a known scheme.

The reconstruction from the RHH can be obtained using the same equations (1, 2, 3) with the superscript L replaced by R. The final image reconstruction of the double-helix trajectory, $\hat{f}(\underline{x})$, can be obtained as the sum of $\hat{f}^L(\underline{x})$ and $\hat{f}^R(\underline{x})$ according to equation 4:

$$\hat{f}(\underline{x}) = \hat{f}^L(\underline{x}) + \hat{f}^R(\underline{x}) \quad (4)$$

Figure 11:
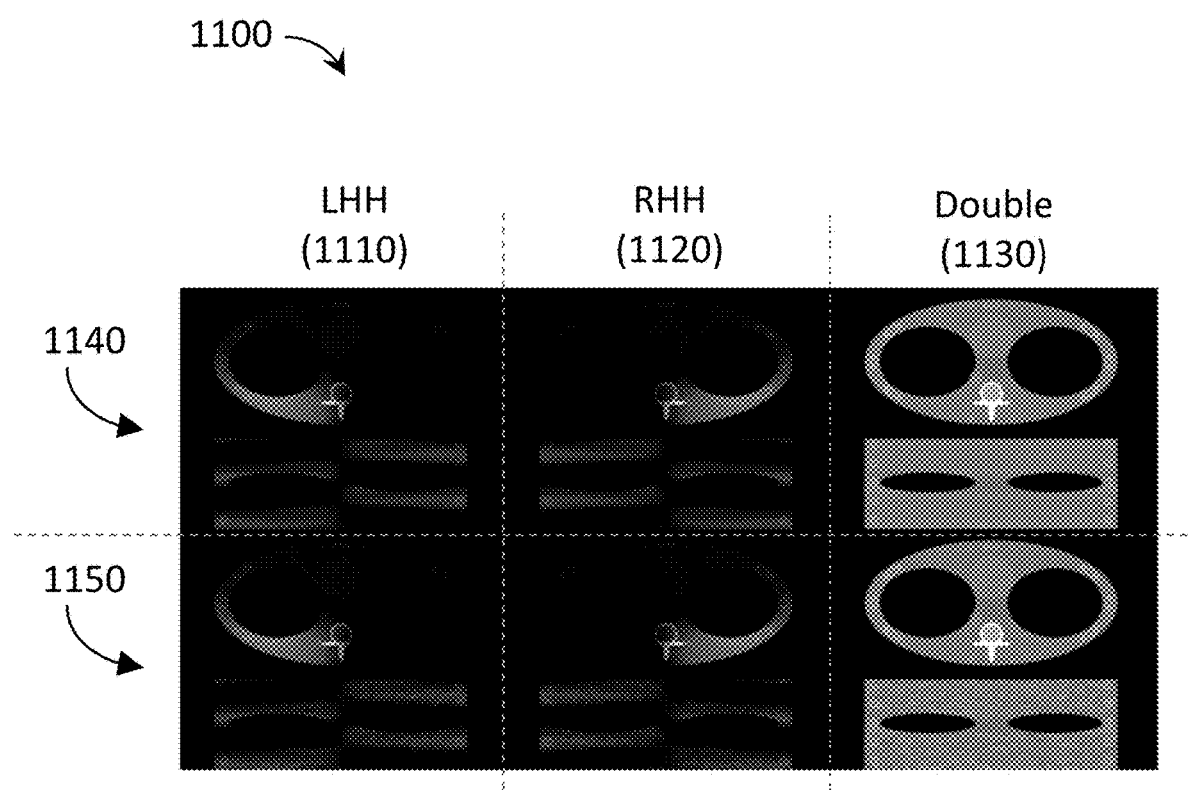
FIG. 11 shows exemplary reconstructions of a thorax phantom using the scans shown in FIGS. 9A and 9B.

FIG. 11 shows exemplary reconstructions 1100 of a thorax phantom using the double-helix scan design and reconstruction technique described above using a computer simulation. In particular, 1110 is the reconstruction of the left-handed helix (LHH), 1120 is the reconstruction of the right-handed helix (RHH), and 1130 is the reconstruction of the double helix. 1140 is the noiseless data and 1150 is the noisy data. The display window is 1000 HU. In this example embodiment, computer simulations were performed using a modified version of the FORBILD thorax phantom. The SID and SDD were 1080 mm and 1620 mm, respectively. The detector 34 consisted of 480 channels and 120 rows with pixel size of [0.9 mm, 0.9 mm]. The detector 34 was symmetric about the u axis and was off-centered along the u axis. The channel offsets were set to 49.75 and 429.75 for the RHH and LHH, respectively. The starting view angles for the LHH and RHH were 0 and π, respectively. Both helices consisted of 3 rotations with a longitudinal range of 216 mm. For each detector pixel, the line integral was calculated as the average of four rays through its corners. Both the LHH and RHH used 480 views per rotation with pitch of 1. Poisson noise (using 55k photon counts) and electronic noise (using 5 counts) were added to the projection data. For image reconstruction, the resolution parameter ε was set to 0.05. Image voxels were isotropic with edge size of 1 mm. These reconstruction results demonstrate that the reconstruction algorithm is able to recover the FORBILD thorax phantom with satisfactory image quality.

In this manner, a double-helix trajectory for imaging, including CBCT during IGRT, can be reconstructed. Compared to a single helix with laterally off-centered detector, the double-helix trajectory can improve data availability, improve scan speed, and reduce image noise. The relation of the configurations between the two helices can significantly impact the data availability and should be optimized.

The included flow charts and block diagrams illustrate exemplary configurations and methodologies associated with multi-pass imaging scan in accordance with the systems described herein. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 12:
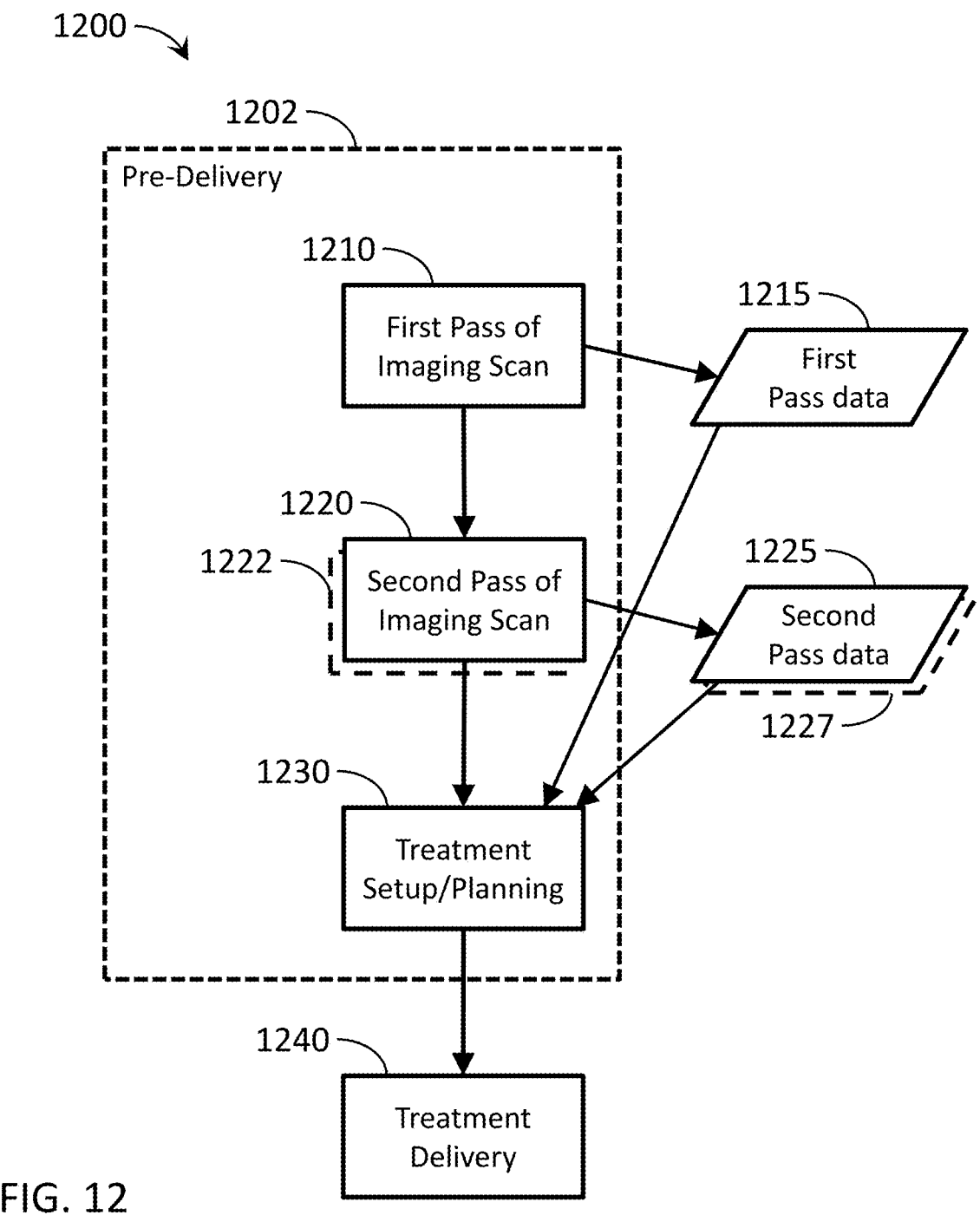
FIG. 12 is a flow chart of an exemplary multi-pass imaging process.

FIG. 12 is a flow chart of an exemplary multi-pass imaging process 1200. Process 1200 can utilize the imaging systems and scan designs described above. Exemplary pre-delivery steps of a workflow are shown as 1202. In this embodiment, an imaging scan is comprised of at least two passes, with each pass acquiring a portion of the data needed by the full imaging scan. Each pass can be executed faster than a full scan. At step 1210, the system executes a first pass of the imaging scan (e.g., while moving the patient support into the gantry), generating first pass data 1215. At step 1220, the system executes a second pass of the imaging scan (e.g., while moving the patient support out of the gantry), generating second pass data 1225.

In this embodiment, the system can process (e.g., reconstruct) the first pass data 1215 generated/received during the first pass 1210 while the system executes the second pass 1220. Next, at step 1230, the system can proceed with various data/image processing and image-based pre-delivery steps (see, e.g., FIGS. 16-18 below) including treatment setup (e.g., reconstruction, registration, alignment, etc.) and treatment planning (e.g., dose calculation, adaptive planning, etc.). In this manner, the pre-delivery steps 1202 can be completed sooner with a multi-pass imaging scan (relative to a single pass scan) since image processing of the first pass data 1215 can occur during the second pass 1220 and since the time associated with returning the patient support from inside the gantry can be utilized as scan time in 1220. After treatment setup/planning 1230 is complete, the process can continue to treatment delivery at step 1240, including as part of IGRT.

In one embodiment, the first pass 1210 can comprise a first tube energy of the imaging radiation source and the second pass 1220 can comprise a second tube energy of the imaging radiation source. The first pass data 1215 can be reconstructed into a first patient image and the second pass data 1225 can be reconstructed into a second patient image such that combining the reconstructed first and second patient images yields a spectral patient image usable for various treatment setup and treatment planning tasks, as described above.

In other embodiments, the imaging scan is comprised of more than the two passes 1210, 1220. Optional additional pass(es) 1222 and additional associated pass data 1227 are shown in FIG. 12 to represent that the imaging scan in these embodiments can include any number of scan passes.

Figure 13:
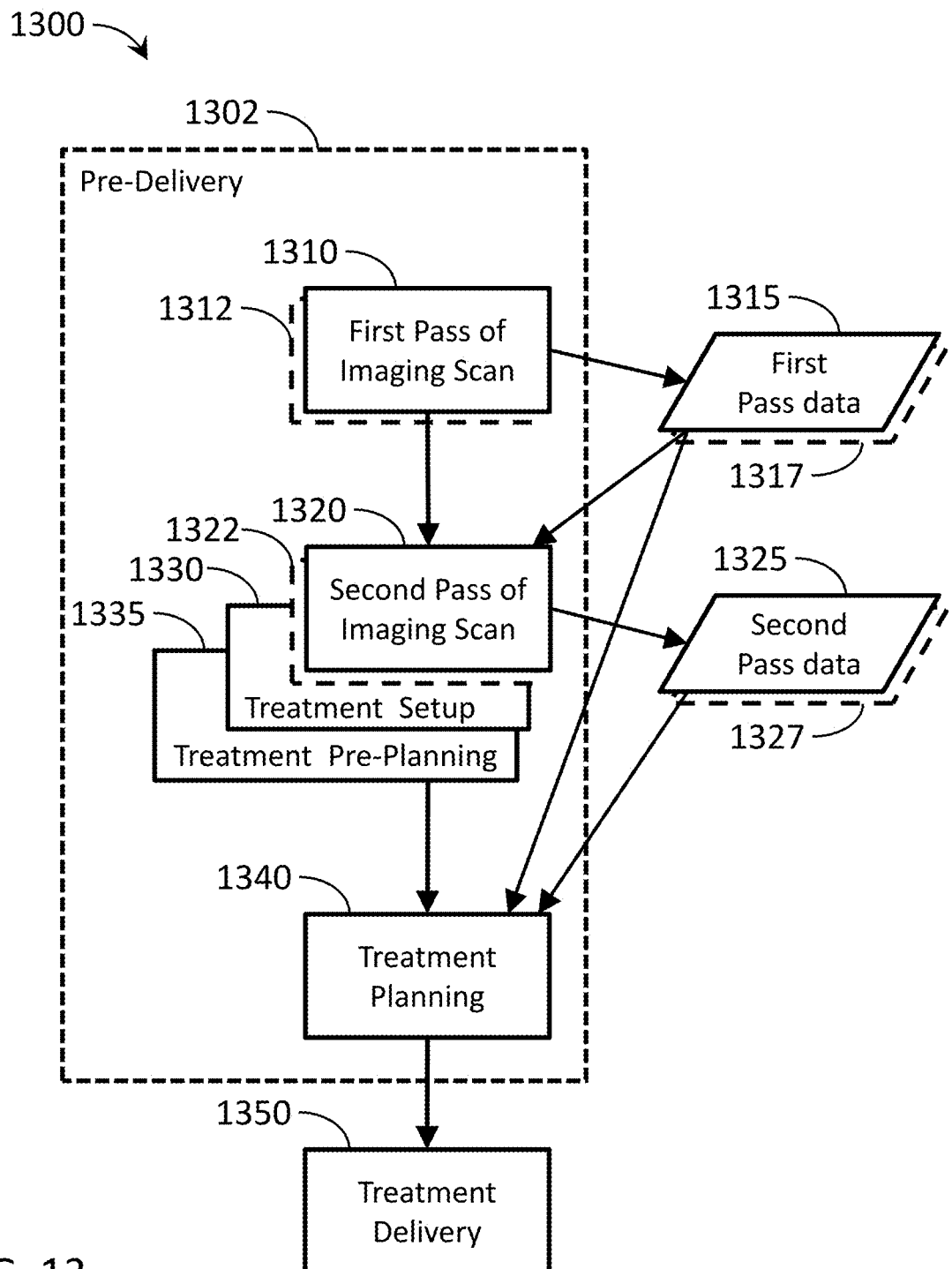
FIG. 13 is a flow chart of another exemplary multi-pass imaging process.

FIG. 13 is a flow chart of another exemplary multi-pass imaging process 1300. Process 1300 can utilize the imaging systems and scan designs described above. Exemplary pre-delivery steps of a workflow are shown as 1302. In this embodiment, an imaging scan is comprised of at least two passes, with each pass acquiring a portion of the data needed by the full imaging scan. Each pass can be executed faster than a full scan. At step 1310, the system executes a first pass of the imaging scan (e.g., while moving the patient support into the gantry), generating first pass data 1315. In this embodiment, the system can utilize the first pass data 1315 generated/received during the first pass 1310 before or while the system executes a second pass 1320.

In various embodiments, the raw and/or processed (e.g., reconstructed) first pass data 1315 can be used before or while the system executes the second pass 1320 for determining/adjusting scan parameters associated with the second pass 1320 (as discussed above) and for various data/image processing and image-based pre-delivery steps (see, e.g., FIGS. 16-18 below), including treatment setup 1330 (e.g., reconstruction, registration, alignment, etc. as discussed above), and/or treatment pre-planning 1335 (e.g., any treatment planning activities that can be started and/or based on the first pass data 1315).

At step 1320, the system executes the second pass of the imaging scan (e.g., while moving the patient support out of the gantry), generating second pass data 1325. In this embodiment, the system can start and/or continue to process the first pass data 1315 generated/received during the first pass 1310 while the system executes the second pass 1320.

Next, at step 1340, the system can utilize the first pass data 1315 and/or the second pass data 1325 (generated/received during the first pass 1310 and the second pass 1320, respectively) to proceed with various data/image processing and image-based pre-delivery steps (see, e.g., FIGS. 16-18 below), including treatment planning (e.g., dose calculation, adaptive planning, etc.). In some embodiments, the system can complete tasks at step 1340 that were started at steps 1330 and/or 1335, including for example, treatment pre-planning 1335 that needs second pass data 1325 for final treatment panning 1340.

In this manner, the pre-delivery steps 1302 can be completed sooner with a multi-pass imaging scan (relative to a single pass scan) since image processing and utilization of the first pass data 1315 can occur before and/or during the second pass 1320 and since the time associated with returning the patient support from inside the gantry can be utilized as scan time in 1320. After treatment planning 1340 is complete, the process can continue to treatment delivery at step 1350, including as part of IGRT.

In one embodiment, the first pass data 1315 is of sufficient quality for treatment setup 1330 such that reconstruction and registration of the patient image (based on the first pass data 1315) with prior data is underway and/or completed during the second pass 1320. After the second pass 1320 is complete, the workflow can proceed directly to treatment planning 1340 based on the first pass data 1315 and the second pass data 1325.

In other embodiments, the imaging scan is comprised of more than the two passes 1310, 1320. Optional additional pass(es) 1312, 1322 and additional associated pass data 1317, 1327 are shown in FIG. 13 to represent that the imaging scan in these embodiments can include any number of scan passes at different points in the workflow sequence. Furthermore, in various embodiments, raw and/or processed data from one or more of these passes can be used before or while the system executes a subsequent pass for determining/adjusting scan parameters associated with a subsequent pass and/or various data/image processing and image-based pre-delivery steps, including treatment setup 1330, and/or treatment pre-planning 1335. For example, two passes may be executed, generating pass data, which can be used to determine scan parameters for a subsequent pass, then the next pass may generate pass data that is then used for treatment setup in combination with previous pass data. As can be appreciated, any number of scan passes can generate pass data that can be utilized in various combinations for any of the workflow steps.

Figure 14:
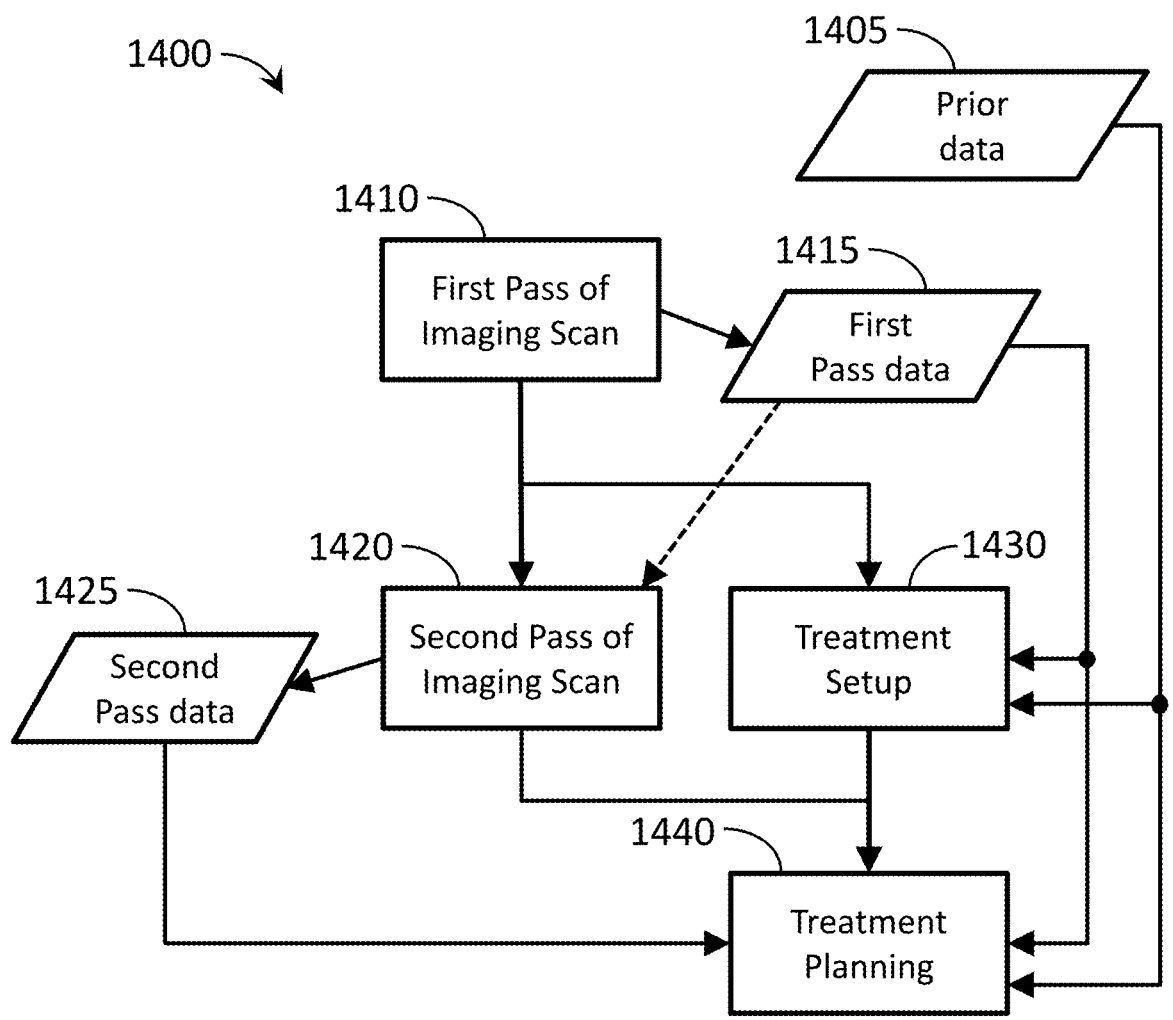
FIG. 14 is a flow chart of another exemplary multi-pass imaging process.

FIG. 14 is a flow chart of another exemplary multi-pass imaging process 1400. Process 1400 can utilize the imaging systems and scan designs described above. In this embodiment, an imaging scan is comprised of at least two passes, with each pass acquiring a portion of the data needed by the full imaging scan. Each pass can be executed faster than a full scan. At step 1410, the system executes a first pass of the imaging scan (e.g., while moving the patient support into the gantry), generating first pass data 1415. In this embodiment, the system can utilize the first pass data 1415 generated/received during the first pass 1410 before or while the system executes a second pass 1420.

In this embodiment, the raw and/or processed (e.g., reconstructed) first pass data 1415 is used for treatment setup 1430 (e.g., registering a first patient image (based on the first pass data 1415) with prior data 1405) before or while the system executes the second pass 1420. Optionally (depicted in FIG. 14 by dashed line), in some embodiments, the raw and/or processed first pass data 1415 can also be used before the system executes the second pass 1420 for determining/adjusting scan parameters associated with the second pass 1320 (as discussed above).

At step 1420, the system executes the second pass of the imaging scan (e.g., while moving the patient support out of the gantry), generating second pass data 1425. In this embodiment, the system can start and/or continue treatment setup 1430 using the first pass data 1415 generated/received during the first pass 1410 while the system executes the second pass 1420.

Next, at step 1440, the system utilizes the first pass data 1415 and the second pass data 1425 for treatment planning (e.g., dose calculation, adaptive planning, etc.). In some embodiments, the prior data 1405 is also utilized for treatment planning 1440 tasks.

In this manner, pre-delivery workflow steps treatment setup 1430 and treatment planning 1440 are completed sooner with the multi-pass imaging scan (1410+1420) than a single pass scan, since treatment setup 1430 utilizes the first pass data 1415 before and/or during the second pass 1420 and since the time associated with returning the patient support from inside the gantry can be utilized as scan time in 1420. After treatment planning 1440 is complete, the process can continue to treatment delivery, including as part of IGRT.

Figure 15:
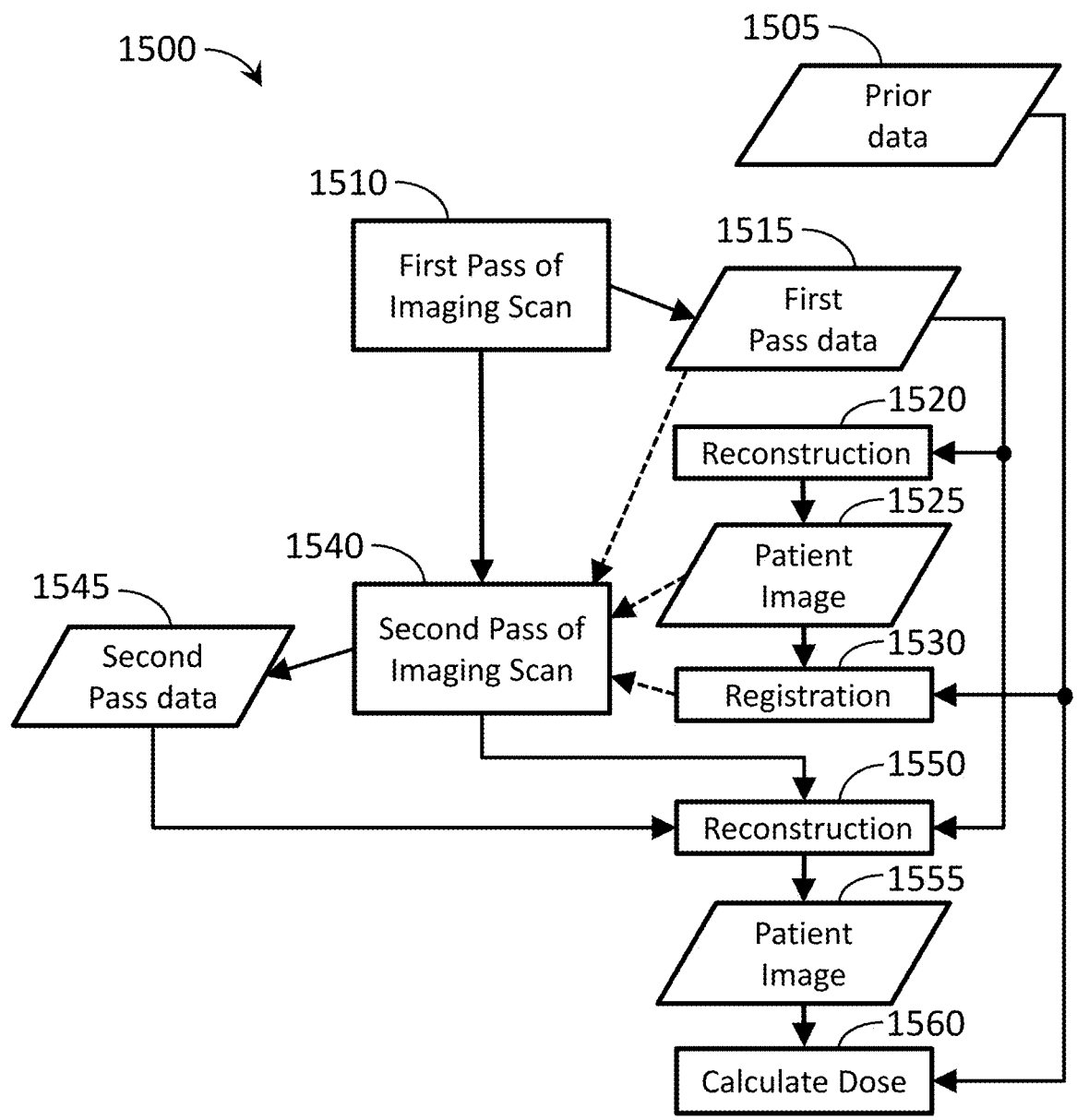
FIG. 15 is a flow chart of another exemplary multi-pass imaging process.

FIG. 15 is a flow chart of another exemplary multi-pass imaging process 1500. Process 1500 can utilize the imaging systems and scan designs described above. In this embodiment, an imaging scan is comprised of at least two passes, with each pass acquiring a portion of the data needed by the full imaging scan. Each pass can be executed faster than a full scan. At step 1510, the system executes a first pass of the imaging scan (e.g., while moving the patient support into the gantry), generating first pass data 1515. In this embodiment, the system can utilize the first pass data 1515 generated/received during the first pass 1510 before or while the system executes a second pass 1520.

In this embodiment, first pass data 1515 is reconstructed at step 1520 using a reconstruction technique suitable for the projection data 1515, generating a patient image 1525. Next, at step 1530, the patient image 1525 is registered with prior image data 1505 for treatment setup before or while the system executes the second pass 1540. Optionally (depicted in FIG. 15 by dashed lines), in some embodiments, projection data 1515, patient image 1525, and/or a registered image from 1530 can also be used before the system executes the second pass 1540 for determining/adjusting scan parameters associated with the second pass 1540 (as discussed above).

At step 1540, the system executes the second pass of the imaging scan (e.g., while moving the patient support out of the gantry), generating second pass data 1545. In this embodiment, the system can start and/or continue reconstruction 1520 and/or registration 1530 using the first pass data 1515 generated/received during the first pass 1510 while the system executes the second pass 1540.

Next, at step 1550, the system utilizes the first pass data 1515 and the second pass data 1545 to reconstruct patient image 1555. At step 1560, the patient image 1555 is utilized to calculate a treatment dose. In some embodiments, the prior data 1505 is also utilized for dose calculation 1560.

In this manner, pre-delivery workflow steps 1520, 1530, 1550, 1560 are completed sooner with the multi-pass imaging scan (1510+1540) than a single pass scan, since reconstruction 1520 and registration 1530 steps utilize the first pass data 1515 before and/or during the second pass 1540 and since the time associated with returning the patient support from inside the gantry can be utilized as scan time in 1540. After dose calculation 1560 is complete, the process can continue to treatment delivery, including as part of IGRT.

In all of these embodiments, various scan designs may be used, including various designs for the passes comprising the imaging scan. For example, as described above, the patient support 18 can move in a first longitudinal direction during the first pass (e.g., into the gantry 12) and move in a second longitudinal direction during the second pass (e.g., out of the gantry 12), where the second direction is opposite the first direction. However, in other embodiments, different passes may be in the same direction. The passes may comprise different patient support 18 and/or gantry 12 speeds, which both may be constant or variable. The passes can also be completed in the same or different times (e.g., where a first pass is completed in less time than a second pass). The passes can also include more or less views than other passes. The pass trajectories can be helical and/or circular (e.g., step-and-shoot, where a series of steps/shoots comprise one pass). Passes can include periods of time when the imaging radiation source is not active, including effectively skipping portions of the patient.

In some embodiments, an axial position of the imaging radiation source 30 and the detector 34 is shifted between passes, including where the data from different passes are complementary during reconstruction of a patient image. In one embodiment, the detector 34 is offset in one transaxial direction during a first pass and offset in an opposite transaxial direction during a second pass, including to accommodate a large FOV.

These techniques can be used for IGRT workflow improvements and optimization and CT image quality and quantitation improvements for dose calculation and adaptive planning.

Figure 16:
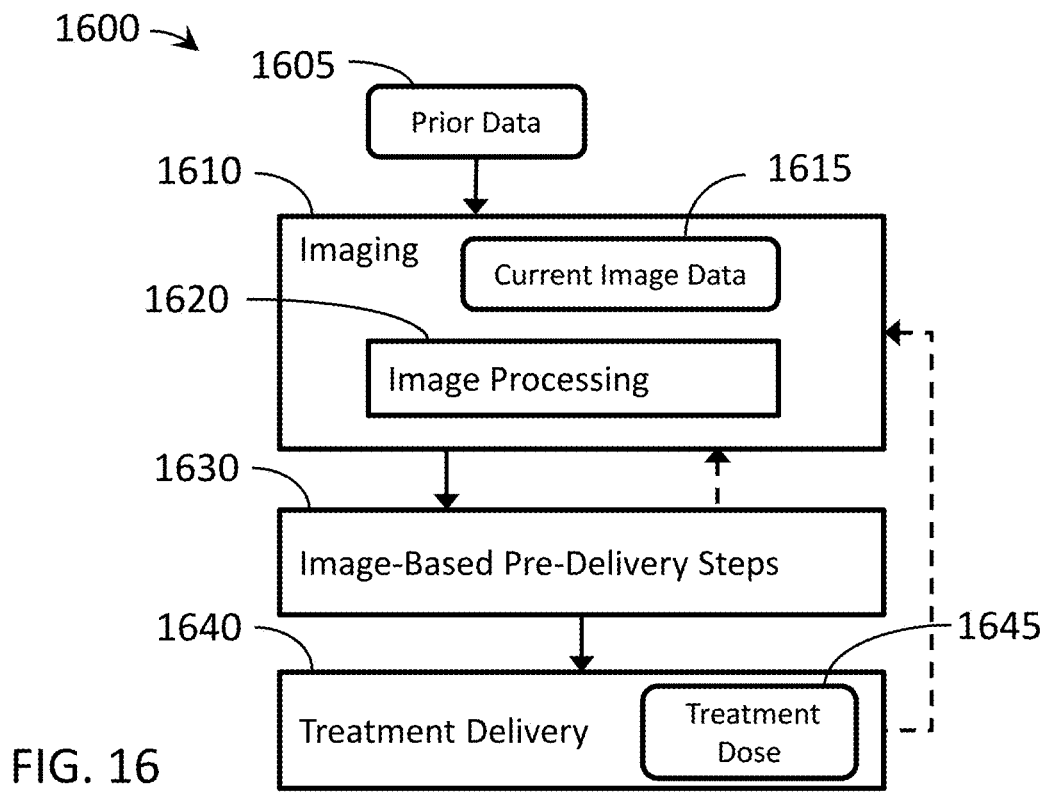
FIG. 16 is a flow chart depicting an exemplary method of IGRT using a radiotherapy device.

FIG. 16 is a flow chart depicting an exemplary method 1600 of IGRT using a radiotherapy device (including, e.g., x-ray imaging apparatus 10). Prior data 1605 can include images of the patient (e.g., a prior image, which may be a previously-acquired planning image, including a prior CT image, as discussed above), treatment plans, phantom information, models, a priori information, etc. In some embodiments, the prior data 1605 is generated by the same radiotherapy device, but at an earlier time. At step 1610, imaging (including multi-pass imaging) of a patient is performed using a source of low-energy radiation (e.g., kV radiation from x-ray source 30). In various embodiments, imaging comprises a helical or circular scan with a fan or cone beam geometry. Step 1610 can produce high-quality (HQ) image(s) or imaging data 1615 using the techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1610 also includes image processing 1620 to generate patient images based on the imaging/scan data 1615 (e.g., in accordance with embodiments described above). Although image processing step 1620 is shown as part of imaging step 1610, in some embodiments image processing step 1620 is a separate step, including where image processing is executed by separate devices.

Next, at step 1630, one or more image-based pre-delivery steps, discussed below, are performed based at least in part on the imaging data 1615 from step 1610. As discussed in more detail below, step 1630 can include determining various parameters associated with the therapeutic treatment and (subsequent) imaging planning. In some embodiments, image-based pre-delivery steps (1630) may require more imaging (1610) before treatment delivery (1640). Step 1630 can include adapting a treatment plan based on the high-quality imaging data 1615 as part of an adaptive radiotherapy routine. In some embodiments, image-based pre-delivery steps 1630 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1640, therapeutic treatment delivery is performed using a source of high-energy radiation (e.g., MV radiation from therapeutic radiation source 20). Step 1640 delivers a treatment dose 1645 to the patient according to the treatment plan. In some embodiments, the IGRT method 1600 may include returning to step 1610 for additional imaging at various intervals, followed by image-based pre-delivery steps (1630) and/or treatment delivery (1640) as required. In this manner the high-quality imaging data 1615 may be produced and utilized during IGRT using one apparatus 10 that is capable of adaptive therapy. As mentioned above, steps 1610, 1630, and/or 1640 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly perform imaging 1610, image-based pre-delivery steps 1630, and treatment delivery 1640, including moving the radiation source according to the treatment plan.

The imaging and processing techniques described above to support quicker pre-delivery workflows, including multi-pass imaging scans, treatment set-up, treatment pre-planning, and treatment planning steps are included in the imaging 1610 and image-based pre-delivery steps 1630 described herein, including as part of an IGRT workflow.

Figure 17:
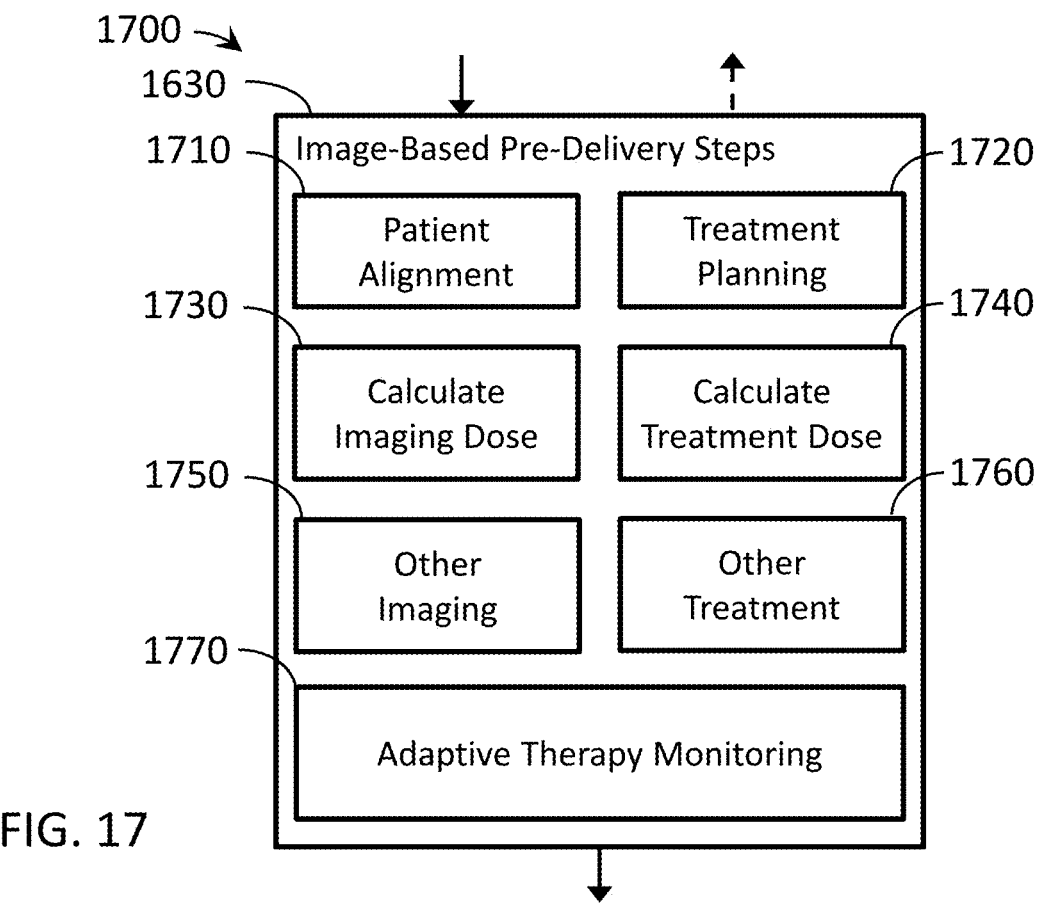
FIG. 17 is a block diagram depicting exemplary image-based pre-delivery steps.

FIG. 17 is a block diagram 1700 depicting exemplary image-based pre-delivery steps/options that may be associated with step 1630 above. It will be appreciated that the above-described x-ray imaging apparatus 10 (e.g., as part of a radiotherapy device) can generate kV images that can be used in a variety of ways, including for image-based pre-delivery steps (1630), without departing from the scope of the present invention. For example, images 1615 generated by the radiotherapy device can be used to align a patient prior to treatment (1710). Patient alignment can include correlating or registering the current imaging data 1615 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the x-ray imaging apparatus 10 can also be used for treatment planning or re-planning (1720). In various embodiments, step 1720 can include confirming the treatment plan, modifying the treatment plan, generating a new treatment plan, and/or choosing a treatment plan from a set of treatment plans (sometimes referred to as "plan of the day"). For example, if the imaging data 1615 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1615 (generated by the x-ray imaging apparatus 10 at step 1610), the imaging data 1615 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the x-ray imaging apparatus 10 can be used to calculate imaging dose (1730), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the x-ray imaging apparatus 10 can be used to calculate treatment dose (1740), which may be used for ongoing determinations of total dose to the patient and/or may be included as part of treatment planning or re-planning.

In accordance with other exemplary use cases, images generated by the x-ray imaging apparatus 10 can be used in connection with planning or adjusting other imaging (1750) and/or other treatment (1760) parameters or plans, including, for example, as part of adaptive therapy and/or treatment plan generation. In accordance with another exemplary use case, images generated by the x-ray imaging apparatus 10 can be used in connection with adaptive therapy monitoring (1770), which can include monitoring treatment delivery and adapting as required.

It should be appreciated that the image-based pre-delivery steps (1630) are not mutually exclusive. For example, in various embodiments, calculate treatment dose (1740) can be a step by itself and/or can be part of adaptive therapy monitoring (1770) and/or treatment planning (1720). In various embodiments, the image-based pre-delivery steps (1620) can be performed automatically and/or manually with human involvement.

The devices and methods described above, including the offset detector and data processing techniques, can provide improved kV-generated images of higher quality than conventional in-treatment imaging systems.

Figure 18:
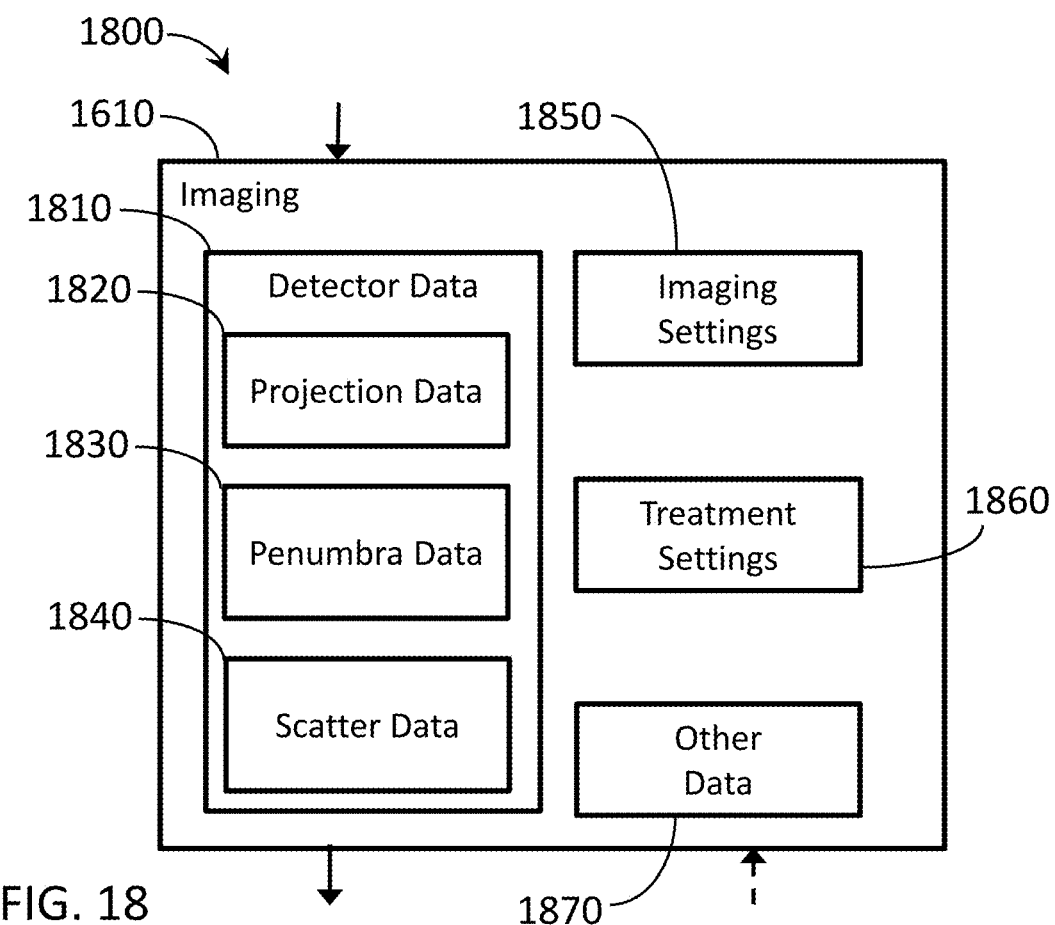
FIG. 18 is a block diagram depicting exemplary data sources that may be utilized during imaging or image-based pre-delivery steps.

FIG. 18 is a block diagram 1800 depicting exemplary data sources that may be utilized during imaging (1610) and/or subsequent image-based pre-delivery steps (1630). Detector data 1810 represents all of the data received by the image radiation detector 34. The projection data 1820 is the data generated by the radiation incident in the collimated beam area. The penumbra data 1830 is the data generated by the radiation incident in the penumbra area. The scatter data 1840 is the data generated by the radiation incident in the peripheral area outside of the penumbra area, which may be referred to as the shadow region(s).

In one embodiment, the penumbra data 1830 may be used to separate or identify the projection and/or scatter data. In some embodiments, the scatter data 1840 can be used to estimate the scatter radiation in the projection data 1820. In another embodiment, the scatter data 1840 can be used to determine the residual effect of the scatter from the therapeutic radiation source 20 (e.g., MV) when the two sources 20, 30 are operated simultaneously or in an interleaved manner.

In this manner, the penumbra data 1830 and/or the scatter data 1840 may be utilized to improve the quality of the images generated by the imaging step 1610. In some embodiments, the penumbra data 1830 and/or the scatter data 1840 may be combined with the projection data 1820 and/or analyzed in view of the applicable imaging settings 1850, treatment settings 1860 (e.g., if simultaneous imaging and treatment radiation), and any other data 1870 associated with the x-ray imaging apparatus 10 at the time of the data collection at the imaging detector 34. In other embodiments, the data may be used for the treatment planning step 1630.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An x-ray imaging apparatus for multi-pass scans, comprising:
   a rotatable gantry system positioned at least partially around a patient support;
   a first radiation source coupled to the rotatable gantry system, the first radiation source configured as an imaging radiation source;
   a radiation detector coupled to the rotatable gantry system and positioned to receive radiation from the first radiation source during an imaging scan;
   a controller configured to:
      move the patient support relative to the rotatable gantry system during a first pass of the imaging scan;
      move the patient support relative to the rotatable gantry system during a second pass of the imaging scan;
   a data processing system configured to:
      receive first imaging data measured by the radiation detector during the first pass;
      receive second imaging data measured by the radiation detector during the second pass;
      combine the first imaging data and the second imaging data into a combined imaging dataset; and
      reconstruct a second patient image using the combined imaging dataset;
   wherein a relative axial position of the first radiation source and the radiation detector is shifted during the second pass relative to the first pass, and wherein the first imaging data and the second imaging data are used jointly during reconstruction of the second patient image.

2. The apparatus of claim 1, wherein the data processing system is further configured to reconstruct a first patient image based on the first imaging data, wherein the first patient image is reconstructed during the second pass.

3. The apparatus of claim 1, wherein a scanning parameter for the second pass is determined based on the first imaging data.

4. The apparatus of claim 3, wherein the data processing system is further configured to reconstruct a first patient image based on the first imaging data, and wherein the first patient image is registered with a planning image to determine the scanning parameter.

5. The apparatus of claim 3, wherein the scanning parameter comprises at least one of a pitch, an energy level, a tube potential, a tube current, a pulse width, a beam filter, or a speed.

6. The apparatus of claim 1, wherein the first pass comprises a first tube energy of the first radiation source and the second pass comprises a second tube energy of the first radiation source, and wherein the second patient image comprises a spectral patient image.

7. The apparatus of claim 1, wherein the data processing system is further configured to reconstruct a first patient image based on the first imaging data, and wherein a treatment setup is based on the first patient image and a treatment plan is based on the second patient image.

8. The apparatus of claim 7, wherein the treatment setup comprises registering the first patient image with a planning image.

9. The apparatus of claim 1, wherein the patient support moves in a first longitudinal direction during the first pass and moves in a second longitudinal direction during the second pass, and wherein the second direction is opposite the first direction.

10. The apparatus of claim 1, wherein the patient support moves at a first speed during the first pass and moves in at a second speed during the second pass, and wherein the first speed is faster than the second speed.

11. The apparatus of claim 1, wherein the first pass and the second pass comprise helical scans.

12. The apparatus of claim 1, wherein the first pass is completed in a first time and the second pass is completed in a second time, and wherein the second time is longer than the first time.

13. The apparatus of claim 1, wherein the second pass comprises more views than the first pass.

14. The apparatus of claim 1, wherein the radiation detector is offset in one transaxial direction during the first pass and offset in an opposite transaxial direction during the second pass.

15. The apparatus of claim 1, further comprising a second radiation source coupled to the rotatable gantry system, the second radiation source configured as a therapeutic radiation source, wherein the second radiation source delivers a dose of radiation calculated based on the second patient image.

16. A method of collecting imaging data during a multi-pass scan, comprising:
   moving a patient support relative to a rotatable gantry system during a first pass of an imaging scan, wherein a first radiation source and a radiation detector are coupled to the rotatable gantry system positioned at least partially around the patient support;
   receiving first imaging data measured by the radiation detector during the first pass;
   moving the patient support relative to the rotatable gantry system during a second pass of the imaging scan;
   receiving second imaging data measured by the radiation detector during the second pass;
   combining the first imaging data and the second imaging data to form a combined imaging dataset;
   reconstructing a patient image using the combined imaging dataset;
   registering the first image with a planning image for treatment setup; and
   calculating a therapeutic radiation dose based on the second patient image.

17. The method of claim 16, wherein the patient support moves in a first longitudinal direction during the first pass and moves in a second longitudinal direction during the second pass, and wherein the second direction is opposite the first direction.

18. A radiotherapy delivery device comprising:
a rotatable gantry system positioned at least partially around a patient support;
a first radiation source coupled to the rotatable gantry system, the first radiation source configured as an imaging radiation source;
a second radiation source coupled to the rotatable gantry system, the second radiation source configured as a therapeutic radiation source
a radiation detector coupled to the rotatable gantry system and positioned to receive radiation from the first radiation source during an imaging scan;
a controller configured to:
   move the patient support relative to the rotatable gantry system during a first pass of the imaging scan;
   move the patient support relative to the rotatable gantry system during a second pass of the imaging scan;
a data processing system configured to:
   receive first projection data measured by the radiation detector during the first pass;
   reconstruct a first patient image based on the first projection data;
   receive second projection data measured by the radiation detector during the second pass; and
   reconstruct a second patient image based on the first projection data and the second projection data;
wherein a treatment setup is based on the first patient image, and wherein the second radiation source delivers a dose of radiation calculated based on the second patient image during adaptive IGRT.

* * * * *